United States Patent [19]

Asselin et al.

[11] 4,309,348

[45] Jan. 5, 1982

[54] TRICYCLIC INDOLE DERIVATIVES

[75] Inventors: Andre A. Asselin, St. Laurent; Leslie G. Humber, Dollard des Ormeaux; Gervais Dionne, St. Laurent; Clara Revesz, Montreal; Amedeo Failli, St. Laurent, all of Canada

[73] Assignee: American Home Products Corporation, New York, N.Y.

[21] Appl. No.: 159,264

[22] Filed: Jun. 13, 1980

Related U.S. Application Data

[62] Division of Ser. No. 38,994, May 14, 1979, Pat. No. 4,235,901, which is a division of Ser. No. 904,081, May 8, 1978, Pat. No. 4,179,503.

[51] Int. Cl.$^3$ .............. C07D 491/056; C07D 495/04
[52] U.S. Cl. .............. 260/326.28; 260/326.29; 260/326.5 SA; 260/326.5 B
[58] Field of Search .............. 260/326.28, 326.29, 260/326.5 SA, 326.5 B

[56] References Cited

U.S. PATENT DOCUMENTS 3,843,681 10/1974 Demerson et al. ........ 260/326.14 R
3,880,853 4/1975 Demerson et al. ........... 260/326.5 B

*Primary Examiner*—John M. Ford
*Assistant Examiner*—R. W. Ramsuer
*Attorney, Agent, or Firm*—Arthur E. Wilfond

[57] ABSTRACT

Indole derivatives characterized by having a 1,3,4,9-tetrahydropyrano[3,4-b]indole or 1,3,4,9-tetrahydrothiopyrano[3,4-b]indole nucleus with a hydroxyalkanamine or lower alkoxyalkanamine substituent and a lower alkyl group at position 1 are disclosed. The nucelus is optionally further substituted at position 9 and on the aromatic ring. The derivatives are useful diuretic agents, and methods for their preparation and use are also disclosed.

7 Claims, No Drawings

TRICYCLIC INDOLE DERIVATIVES

This is a division, of application Ser. No. 38,994, filed May 14, 1979, now U.S. Pat. No. 4,235,906, which is a division of application Ser. No. 904,081, filed May 8, 1978, now U.S. Pat. No. 4,179,503.

BACKGROUND OF THE INVENTION a. Field of the Invention

This invention relates to novel pyranoindole derivatives, to a process and to intermediates for preparing the derivatives, to methods for using the derivatives and to compositions and therapeutically acceptable salts of the derivatives.

More specifically, the present invention relates to novel 1,3,4,9-tetrahydropyrano[3,4-b]indole or 1,3,4,9-tetrahydrothiopyrano[3,4-b]indole derivatives having a hydroxyalkanamine or lower alkoxyalkanamine and a lower alkyl group at position 1. These derivatives are useful as diuretic agents in a mammal at dosages which do not elicit undesirable side effects. The combination of these attributes render the 1,3,4,9-tetrahydro(thio)-pyrano[3,4-b]indole derivatives of this invention therapeutically useful.

The 1,3,4,9-tetrahydro(thio)pyrano[3,4-b]indole derivatives of this invention belong to a special class of diuretic agents which antagonize the renal effects of mineralocorticoids. As a result, these compounds are useful in treating hyperaldosteronism by increasing urine volume and sodium and chloride excretion without affecting potassium excretion. Therefore, these compounds find utility in the treatment of edema and hypertension.

b. Description of the Prior Art

A number of reports dealing with 1,3,4,9-tetrahydro(-thio)pyrano[3,4-b]indole derivatives are available. For instance, a number of these derivatives are reported by C. A. Demerson et al., in U.S. Pat. No. 3,843,681, issued Oct. 22, 1974 and C. A. Demerson et al., in U.S. Pat. No. 3,880,853, issued Apr. 19, 1975.

The compounds of the present invention are distinguished from the compounds of the prior art by the nature of the substituents on the pyranoindole nucleus and by their pharmacologic properties. More specifically, the novel compounds of this invention are distinguished from the prior art compounds by having a hydroxyalkanamine or lower alkoxyalkanamine group at position 1 of the pyranoindole nucleus. In addition, the novel pyrano[3,4-b]indole or thiopyrano[3,4-b]indole derivatives of this invention possess useful diuretic activity in mammals, a pharmacologic activity not previously reported for pyrano[3,4-b]indole derivatives.

SUMMARY OF THE INVENTION

The compounds of this invention are represented by formula I

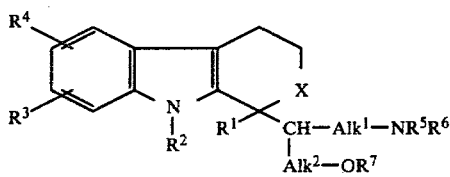

in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; $R^5$ and $R^6$ each independently is hydrogen or lower alkyl or $R^5$ and $R^6$ together with the nitrogen atom to which they are attached form a pyrrol-1-yl, piperidino or morpholino; $R^7$ is hydrogen or lower alkyl; $Alk^1$ and $Alk^2$ each independently is a straight or branched chain lower alkylene having one to six carbon atoms; and X is oxa or thia.

A preferred group of compounds of this invention are represented by formula I in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; $R^5$ and $R^6$ each independently is hydrogen or lower alkyl; $R^7$ is hydrogen or lower alkyl; $Alk^1$ and $Alk^2$ each independently is a straight or branched chain lower alkylene having one to six carbon atoms; and X is oxa.

Another preferred group of compounds of this invention are represented by formula I in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; $R^5$ and $R^6$ each independently is hydrogen or lower alkyl; $R^7$ is hydrogen or lower alkyl; $Alk^1$ and $Alk^2$ each independently is a straight or branched chain lower alkylene having one to six carbon atoms; and X is thia.

Another preferred group of compounds of this invention are represented by formula I in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; $R^5$ and $R^6$ together with the nitrogen atom to which they are attached form a pyrrol-1-yl, piperidino or morpholino; $R^7$ is hydrogen or lower alkyl; $Alk^1$ and $Alk^2$ each independently is a straight or branched chain lower alkylene having one to six carbon atoms; and X is oxa.

Another preferred group of compounds of this invention are represented by formula I in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; $R^5$ and $R^6$ together with the nitrogen atom to which they are attached form a pyrrol-1-yl, piperidino or morpholino; $R^7$ is hydrogen or lower alkyl; $Alk^1$ and $Alk^2$ each independently is a straight or branched chain lower alkylene having one to six carbon atoms; and X is thia.

Another preferred group of compounds of this invention are represented by formula I in which $R^1$ is lower alkyl; $R^2$ is hydrogen or lower alkyl; $R^3$ and $R^4$ each independently is hydrogen, lower alkyl or halo; $R^5$ and $R^6$ each independently is hydrogen or lower alkyl or $R^5$ and $R^6$ together with the nitrogen atom form a pyrrol-1-yl or morpholino; $R^7$ is hydrogen or lower alkyl; $Alk^1$ and $Alk^2$ each independently is a straight chain lower alkylene having one to six carbon atoms; and X is oxa or thia.

Another preferred group of compounds of this invention are represented by formula I in which $R^1$ is lower alkyl; $R^2$ is hydrogen or lower alkyl; $R^3$ and $R^4$ each independently is hydrogen, lower alkyl or halo; $R^5$ and $R^6$ each independently is hydrogen or lower alkyl; $R^7$ is hydrogen or lower alkyl; $Alk^1$ and $Alk^2$ each independently is a straight chain lower alkylene having one to six carbon atoms; and X is oxa.

Another preferred group of compounds of this invention are represented by formula I in which $R^1$ is lower alkyl; $R^2$ is hydrogen or lower alkyl; $R^3$ and $R^4$ each independently is hydrogen, lower alkyl or halo; $R^5$ and $R^6$ together with the nitrogen atom form a pyrrol-1-yl or morpholino; $R^7$ is hydrogen or lower alkyl; $Alk^1$ and $Alk^2$ each independently is a straight chain lower alkylene having one to six carbon atoms; and X is oxa.

Another preferred group of compounds of this invention are represented by formula I in which $R^1$ is lower alkyl; $R^2$ is hydrogen or lower alkyl; $R^3$ and $R^4$ each independently is hydrogen, lower alkyl or halo; $R^5$ and $R^6$ each independently is hydrogen or lower alkyl; $R^7$ is hydrogen or lower alkyl; $Alk^1$ and $Alk^2$ each independently is a straight chain lower alkylene having one to six carbon atoms; and X is thia.

Another preferred group of compounds of this invention are represented by formula I in which $R^1$ is lower alkyl; $R^2$ is hydrogen or lower alkyl; $R^3$ and $R^4$ each independently is hydrogen, lower alkyl or halo; $R^5$ and $R^6$ together with the nitrogen atom form a pyrrol-1-yl or morpholino; $R^7$ is hydrogen or lower alkyl; $Alk^1$ and $Alk^2$ each independently is a straight chain lower alkylene having one to six carbon atoms; and X is thia.

A most preferred group of compounds of this invention are represented by formula I in which $R^1$ and $R^5$ are lower alkyl; $R^2$ and $R^6$ each independently is hydrogen or lower alkyl; $R^3$, $R^4$ and $R^7$ are hydrogen; $Alk^1$ is $CH_2$; $Alk^2$ is $(CH_2)_2$; and X is oxa.

The compounds of formula I in which $R^1$, $R^2$, $R^3$, $R^4$, $R^5$, $R^6$, $R^7$, X, $Alk^1$ and $Alk^2$ are as defined herein are prepared by a process which comprises:

condensing a compound of formula II

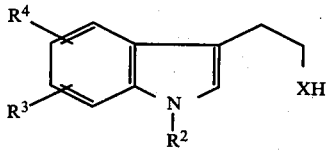

in which $R^2$, $R^3$, $R^4$ and X are as defined herein with a ketone of formula III $$R^1-CO-CHYZ \qquad (III)$$

in which $R^1$ is as defined herein; Y is selected from the group consisting of:

a. $COOR^8$ wherein $R^8$ is hydrogen or lower alkyl, or a radical of formula $Alk^3-COOR^8$ wherein $Alk^3$ is a straight or branched chain lower alkylene having one to five carbon atoms and $R^8$ is hydrogen or lower alkyl;

b. $CONR^5R^6$ wherein $R^5$ and $R^6$ are as defined herein, or a radical of formula $Alk^3-CONR^5R^6$ wherein $Alk^3$. $R^5$ and $R^6$ are as defined herein;

c. a radical of formula $Alk^1-NR^5-COR^9$ wherein $Alk^1$ and $R^5$ are as defined herein and $R^9$ is hydrogen or lower alkyl having one to five carbon atoms;

d. a radical of formula $Alk^1$-halo wherein $Alk^1$ is as defined herein and halo is chloro, bromo or iodo;

e. a radical of formula $Alk^1-NO_2$ wherein $Alk^1$ is as defined herein; and f. a radical of formula $Alk^1-NR^5R^6$ wherein $Alk^1$, $R^5$ and $R^6$ are as defined herein;

and Z is selected from the group consisting of:

a. $COOR^{10}$ wherein $R^{10}$ is hydrogen or lower alkyl, or a radical of formula $Alk^4-COOR^{10}$ wherein $Alk^4$ is a straight or branched chain lower alkylene having one to five carbon atoms and $R^{10}$ is as defined herein;

b. a radical of formula $Alk^2-OCOR^{11}$ wherein $Alk^2$ is a defined herein and $R^{11}$ is lower alkyl; and c. a radical of formula $Alk^2-OR^7$ wherein $Alk^2$ and $R^7$ are as defined herein; with the proviso that when Y is a radical of formula $Alk^1-NR^5R^6$ then Z is selected from the group consisting of $COOR^{10}$, $Alk^4-COOR^{10}$ and $Alk^2-OCOR^{11}$; in the presence of an acid catalyst to obtain the corresponding compound of formula IV

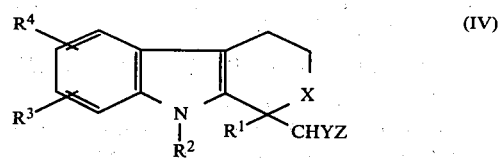

in which $R^1$, $R^2$, $R^3$, $R^4$, X, Y and Z are as defined herein, and subjecting the compound of IV in optional order and to the extent required to alkylation and reduction.

The therapeutically acceptable acid addition salts of the compounds of formula I are included within the scope of this invention.

A compound of formula I or a therapeutical acceptable acid addition salt thereof increases the excretion of urine (diuresis) in a mammal, antagonizes renal mineralocorticoid in a mammal, increases the excretion of urine in a mammal without excessive loss of potassium, reverses or prevents secondary aldosteronism and potassium depletion induced in a mammal undergoing diuretic therapy, and is useful for treating hypertension.

A compound of formula I, or a therapeutically acceptable salt thereof, and a pharmaceutically acceptable carrier forms a pharmaceutical composition.

In addition, a compound of formula I, or a therapeutically acceptable salt thereof, in combination with a non-mineralocorticoid antagonizing diuretic agent and a pharmaceutically acceptable carrier forms a pharmaceutical composition.

DETAILED DESCRIPTION OF THE INVENTION

The term "lower alkyl" as used herein means straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "lower alkylene" as used herein means a divalent organic radical derived from either straight and a branched chain aliphatic hydrocarbons, containing from one to six carbon atoms by removal of two hydrogen atoms and includes methylene, ethylene, 1-methylpropylene, 2-ethylpropylene, 2-butylethylene and the like.

The term "lower alkanoyl" as used herein means straight chain alkanoyl radicals containing from two to seven carbon atoms and a branched chain alkanoyl radical containing four carbon atoms and includes acetyl, propionyl, isobutyryl, hexanoyl, heptanoyl and the like.

The term "halo" as used herein means halogens and includes fluorine, chlorine, bromine and iodine, unless stated otherwise.

The term "inorganic proton acceptor" as used herein means the inorganic bases, preferably the alkali metal hydroxides, carbonates, hydrides, amides and alkoxides, for example, sodium ethoxide, sodium hydroxide, potassium hydroxide, potassium carbonate, sodamide, sodium methoxide, sodium hydride and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid, the organic acids, e.g. maleic, citric, or tartaric acid, and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers contained therein. It is to be understood that the diastereomers arising from such asymmetry are included within the scope of this invention. Such diastereomers are obtained in substantially pure form by classical separation techniques and by sterically controlled synthesis and have arbitrarily been named as isomers A and B, respectively.

Individual optical enantiomers, which might be separated by fractional crystallization of the diasteromeric salts thereof, for instance, salts with d- or l-tartaric acid or D-(+)-α-bromocamphor sulfonic acid, are also included.

The compounds of this invention of formula I or a therapeutically acceptable salt thereof are useful diuretic agents in a mammal upon oral or parenteral administration.

The compounds of formula I are shown to be effective diuretic agents in mammals by tests conducted in dogs or rats. An example of such a test for diuretic agents in rats is described by J. R. Cummings et al., J. Pharmacol. Exp. Ther., 414, 128 (1960). In this test, the urine of the rats is collected for five hours, during which time food and water are withdrawn. Urine volumes as well as sodium, potassium and chloride ion concentrations are determined. The compounds of this invention exhibit a dose- response dependency when they are orally administered in dosages ranging from 50 to 300 mg per kilogram of body weight. For example, the following representative compounds of formula I are effective diuretic agents when administered to the rat (the effective oral dose in mg per kilogram of body weight to obtain a three fold increase in urine volume and/or electrolyte concentration is indicated within the parentheses): γ-[(dimethylamino)methyl]-1,3,4,9-tetrahydro-1-methyl-pyrano[3,4-b]indole-1-propanol, isomer B, (150 mg, described in Example 3), γ-[(dimethylamino)methyl]-5-chloro-1-methyl-1,3,4,9-tetrahydropyrano[3,4-b]indole-1-propanol, isomer A, (150 mg, described in Example 4), γ-(pyrrolidin-1-ylmethyl)-1-methyl-1,3,4,9-tetrahydropyrano[3,4-b]indole-1-propanol (100 mg, described in Example 9), γ-[(dimethylamino)methyl]-1,9-dimethyl-1,3,4,9-tetrahydropyrano[3,4-b]indole 1-propanol (100 mg, described in Example 36) and N,N-dimethyl-4-methoxy-2-(1,9-dimethyl-1,3,4,9-tetrahydropyrano[3,4-b]indol-1-yl)-butanamine (150 mg, described in Example 37).

In addition to the above test for diuretic activity, the compounds of formula I antagonize the renal actions of mineralocorticoids and thus cause an increase in sodium and chloride excretion without affecting potassium excretion.

Aldosterone is a naturally occuring mineralocorticoid of the adrenal cortex which promotes the reabsorption of sodium and chloride and the excretion of potassium, hydrogen and ammonium ions in the distal renal tubules. Hyperaldosteronism is found in a number of pathological conditions. Hyperaldosteronism can be corrected by the administration of a diuretic agent which antagonize, the renal action of aldosterone.

Antialdosterone activity can be demonstrated in standard test systems. One such test is described by C. M. Kagawa et al., J. Pharm. Exp. Ther., 126, 123 (1959). In this test male albino rats (150–160 g) are kept under laboratory conditions for four days, after which they are bilaterally adrenalectomized under diethyl ether anesthesia. The animals are then maintained for 48 hours on a diet of Purine Rat Chow and 5% (W/V) glucose solution (ad libitum). Prior to the test the animals are starved for eighteen hours, but are allowed access to the 5% (W/V) glucose solution. Each rat then receives a single subcutaneous injection of physiological saline (2.5 ml) followed by a subcutaneous injection of desoxycorticosterone acetate (DOCA, 12.5 meg per rat). The test compound is administered orally. The rats are placed in metabolism cages and the urine is collected for four hours. Urine volume and urinary sodium, potassium and chloride are measured. In this test the compounds of this invention are effective by showing a dose response dependency in the range of 3 to 100 mg/kg of body weight. More specifically, this test shows that the following representative compounds of formula I are effective diuretic agents by increasing the urine volume and sodium and chloride excretion when administered to the rat (the effective oral dose in mg per kilogram of body weight to obtain a statistically significant increase in urine volume and sodium and chloride concentration is indicated in the parenthesis): γ-[(dimethylamino)methyl]-1,3,4,9-tetrahydro-1-methyl-pyrano[3,4-b]indole-1-propanol, isomer A, (6 mg, described in Example 3), γ-[(dimethylamino)methyl]-5-chloro-1-methyl-1,3,4,9-tetrahydropyrano[3,4-b]indole-1-propanol, isomer A, (50 mg, described in Example 4), γ-(morpholin-4-ylmethyl)-1-methyl-1,3,4,9-tetrahydropyrano[3,4-b]indole-1-propanol (50 mg, described in Example 8). γ-[(methylamino)methyl]-1,3,4,9-tetrahydro-1-methylpyrano[3,4-b]indole-1-propanol (50 mg, described in Example 34), γ-[(dimethylamino)methyl]-1,9-dimethyl-1,3,4,9-tetrahydropyran[8,4-indole-1-propanol (50 mg, described in Example 36) and N,N-dimethyl-4-methoxy-2-(1,9-dimethyl-1,3,4,9-tetrahydropyrano[3,4-b]indole-1-ylbutanamine (50 mg, described in Example 37).

Another test for antialdosterone diuretic activity, described by C. M. Kagawa et al., Arch. Pharmacodyn.

Ther., 149, 8 (1964), is conducted in intact female dogs. The dogs are given 0.25 mg of DOCA in 0.25 ml of sesame oil intramuscularly and the test drug orally by capsule two hours before the beginning of infusion. A retention catheter is placed in the bladder for urine collection, and the cephalic vein is cannulated for infusion. Saline, 0.45%, plus dextrose, 5%, is infused intravenously at a rate of 1 ml/kg/min for 20 minutes, after which the rate is reduced to 0.3 ml/kg/min for the duration of the experiment. Urine is collected at 30 minute intervals, the urine volumes are recorded, and samples are taken. Collections are continued for five 30 minute periods. The urine samples are analyzed and the urinary Na/K ratios are calculated. This test shows that the following compounds of formula I are effective diuretic agents by increasing urine volume and sodium and chloride excretion when administered to the dog (the effective oral dose in mg per kilogram of body weight to obtain a statistically significant increase in urine volume and sodium and chloride concentration is indicated in the parenthesis): γ-[(dimethylamino)methyl]-1,3,4,9-tetrahydro-4-methyl-pyrano[3,4-b]indole-1-propanol, isomer A, (10 mg, described in Example 3) and γ-[(methylamino)methyl]-1,3,4,9-tetrahydro-1-methylpyrano[3,4-b]indole-1-propanol (15 mg, described in Example 34).

The compounds of formula I are also administered to a mammal in a combination with a therapeutically effective dose of a diuretic agent, acting by another mechanism. These latter diuretics, non-renal mineral corticoid antagonizing diuretics, cause loss of water as well as the electrolytes sodium, potassium, etc. Suitable diuretics for this combination, together with their daily dosage, are set out below:

| Diuretic | Recommended daily human dosage range (mg/70 Kg) |
|---|---|
| hydrochlorothiazide | 25–100 |
| chlorothiazide | 500–1000 |
| chlorthalidone | 50–200 |
| ethacrynic acid | 50–200 |
| furosemide | 40–80 |
| quienthazone | 50–100 |
| bumetanide | 1–2 |

The following method illustrates that the combination of the compound of formula I with a diuretic agent results in a useful reduction of potassium excretion.

Male albino Sprague-Dawley rats weighing 180 to 220 g are divided into four groups of seven rats each. At the beginning of the test the bladder of each rat is emptied by gentle suprapubic pressure. The required dose of the compound of formula I and/or diuretic agent is suspended in 2% (W/V) starch solution and administered orally. The control group receives the vehicle only. Each rat receives 5 ml of 0.9% sodium chloride per 100.0 gram of body weight orally. The rats are placed in individual metabolism cages and urine is collected for five hours after which the bladder is again emptied by gentle suprapubic pressure. All urine samples are analyzed for Na, K and Cl content and Na/K ratios are calculated. The results obtained with the combination of the representative compound of formula I, γ-[(dimethylamino)-methyl]-1,3,4,9-tetrahydro-1-methylpyrano[3,4-b]indole-1-propanol, isomer A, (described in Example 3) and the diuretic agent, hydrochlorothiazide, are presented in Table 1. In Table 1, isomer A refers to the compounds, γ-[(dimethylamino)-methyl]-1,3,4,9-tetrahydro-1-methylpyrano[3,4-b]indole-1-propanol, isomer A.

TABLE 1

| Treatment | Oral Dose mg/Kg | Urine Volume (5 hr) ml/rat | Urinary Electrolytes mEg/urine volume | | | Na/K ratio |
|---|---|---|---|---|---|---|
| | | | Na | K | Cl | |
| Vehicle | — | 4.09 ±0.30 | 0.61 ±0.06 | 0.46 ±0.04 | 0.76 ±0.07 | 1.32 ±0.07 |
| hydrochlorothiazide | 100 | 10.10* ±0.87 | 1.40* ±0.14 | 0.67* ±0.04 | 1.59* ±0.07 | 2.13* ±0.14 |
| isomer A | 50 | 8.31* ±0.74 | 1.13* ±0.07 | 0.50 ±0.01 | 1.22* ±0.06 | 2.27* ±0.10 |
| hydrochlorothiazide + isomer A | 100 + 50 | 11.50* ±0.41 | 1.63* ±0.08 | 0.56 ±0.05 | 1.69* ±0.07 | 3.21* ±0.22 |

*P 0.05 statistically different vs control

The combination of a compound of formula I with other diuretic agents is useful for treating certain disease states, for instance, secondary hyperaldosteronism, as a result of pathologic conditions such as ascites due to cirrhosis of the liver. In addition, the use of a compound of formula I, given sequentially or simultaneously, in combination with another diuretic agent can allow the reduction of the usual therapeutic dose of the other diuretic and still cause sufficient sodium excretion without excessive potassium loss.

The above described test methods for diuretic activity illustrate that the diuretic effect of the compounds of formula I is primarily due to the antagonism of mineralocorticoids on renal electrolyte excretion and in part results from an additional direct renal tubular effect. From the above test methods, the compounds of formula I exhibit a separation of diuretic and antialcosterone diuretic activities by posessing effective antialdosterone diuretic activity at lower doses than required for effective diuretic activity. Furthermore, the compounds of formula I, when tested as described above, are nontoxic when administered in effective diuretic and antialdesterone diuretic amounts. In addition, since the compounds of formula I are non-steroidal, the compounds of formula I do not exhibit the undesirable side effects of steroidal antagonists of mineralocorticoids. Such common side effects of steroidal antagonists are gynecomastia, impotence and irregular menses.

In addition to their use as diuretic agents, the compounds of formula I or a therapeutically acceptable acid addition salt thereof are useful agents for the treatment of hypertension in a mammal. For the treatment of hypertension in a mammal, the compounds of formula I are administered in the same manner as described herein for their use as diuretic agents. When used for the treatment of hypertension, the compound of formula I can be administered alone or administered sequentially or simultaneously in combination with an effective amount of a nonmineralocorticoid antagonizing diuretic agent. Furthermore, a combination of an antihypertensive effective amount of an antihypertensive agent with the compound of formula I, or a therapeutically acceptable acid addition salt thereof; or a combination of an antihypertensive effective amount of an antihypertensive agent with the compound of formula I, or a therapeutically acceptable acid addition salt thereof, and an effective amount of a nonminerlocorticoid antagonizing diuretic agent is useful for the treatment of hypertension in a mammal. Suitable antihypertensive agents for use in this combination can be selected from Rauwolfia and related alkaloids e.g. reserpine, syrosingopine, deserpidine, rescinnamine; guanethidines, e.g. guanethidine, 2-heptamethylineimino-ethylguanidine or related guanidines covered in U.S. Pat. No. 2,928,829 by R. P. Mull, issued Mar. 15, 1960, herein incorporated by reference; veratrum alkaloids, e.g. protoveratrines A and B or germine; hydralazine; diazoxide; minoxidil; nitroprusside; phentolamine; phenoxybenzamine; pargyline; chlorisondamine; hexamethonium; mecamylamine; pentoliniuim; trimethaphan; clonidine; methyldopa; and propranolol. A combination of antihypertensive agents, for example reserpine and hydralazine, can be substituted for a single antihypertensive agent, as described above. Suitable methods of administration, compositions and dosages of the above described antihypertensive agents are described in medical textbooks, for instance, see Charles E. Baker, Jr. "Physician's desk reference", Medical Economics Company, Oradell, N.J., 1977. For example, the antihypertensive agent propranolol is administered orally as propranolol hydrochloride (INDERAL) to humans in the effective dose range of 80 to 640 mg per day. The compounds of formula I, when administered in combination with an antihypertensive agent or an antihypertensive agent plus a non-mineralocorticoid antagonizing diuretic agent for the treatment of hypertension, are used in the same manner as described herein for their use as diuretic agents.

When the compounds of formula I of this invention are used as diuretic and/or antialdosterone agents in mammals, e.g. rats and dogs, they are used alone or in combination with pharmacologically acceptable carriers, the proportion of which is determined by the solubility and chemical nature of the compound, chosen route of administration and standard biological practice. For example, they are administered orally in solid form i.e. capsule or tablet. They are also administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspension can also contain one or more preservatives, one or more colouring agents and/or one or more sweetening agents.

Non-aqueous suspensions can be formulated by suspending the active ingredient in a vegetable oil, for example, arachic oil, olive oil, sesame oil, or coconut oil; or in a mineral oil. The suspension can contain a thickening agent, for example beeswax, hard paraffin or cetyl alcohol. These compositions can also contain a sweetening agent, flavouring agent and antioxidant.

The dosage of the compounds of formula I of this invention as diuretic and antialdosterone agents will vary with the form of administration and the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective diuretic and antialdosterone amount of the compounds usually ranges from about 1.0 mg to about 500 mg per kilogram of body weight per day, although as aforementioned variations will occur. However a dosage level that is in range of from about 5 mg to about 300 mg per kilogram of body weight per day is employed most desirably in order to achieve effective results.

Process

For the preparation of the 1,3,4,9-tetrahydro(thio)-pyrano[3,4-b]indole derivatives of this invention we prefer to use as starting materials the indoles of formula II

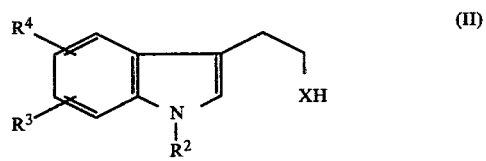

in which $R^2$, $R^3$, $R^4$ and X are as defined herein. The starting materials of formula II are either known or they may be obtained by methods described by C. A. Demerson et al., in U.S. Pat. No. 3,843,681, issued Oct. 22, 1974.

The first step in one embodiment of the process for preparing the compounds of formula I is the condensation of the compound of formula II with a ketone of formula III $$R^1-CO-CHYZ \qquad (III)$$

in which $R^1$ is as defined herein, Y is selected from the group consisting of:

a. $COOR^8$ wherein $R^8$ is hydrogen or lower alkyl, or a radical of formula $Alk^3$-$COOR^8$ wherein $Alk^3$ is a straight or branched chain lower alkylene having one to five carbon atoms and $R^8$ is hydrogen or lower alkyl;

b. $CONR^5R^6$ wherein $R^5$ and $R^6$ are as defined herein, or a radical of formula $Alk^3$-$CONR^5R^6$ wherein $Alk^3$, $R^5$ and $R^6$ are as defined herein;

c. a radical of formula $Alk^1$-$NR^5$-$COR^9$ wherein $Alk^1$ and $R^5$ are as defined herein and $R^9$ is hydrogen or lower alkyl having one to five carbon atoms;

d. a radical of formula $Alk^1$-halo wherein $Alk^1$ is as defined herein and halo is chloro, bromo or iodo;

e. a radical of formula $Alk^1$-$NO_2$ wherein $Alk^1$ is as defined herein; and f. a radical of formula $Alk^1$-$NR^5R^6$ wherein $Alk^1$, $R^5$ and $R^6$ are as defined herein;

and Z is selected from the group consisting of:

a. $COOR^{10}$ wherein $R^{10}$ is hydrogen or lower alkyl, or a radical of formula $Alk^4$-$COOR^{10}$ wherein $Alk^4$ is a straight or branched chain lower alkylene having one to five carbon atoms and $R^{10}$ is as defined herein;

b. a radical of formula Alk$^2$-OCOR$^{11}$ wherein Alk$^2$ is as defined herein and R$^{11}$ is lower alkyl; and c. a radical of formula Alk$^2$-OR$^7$ wherein Alk$^2$ and R$^7$ are as defined herein with the proviso that when Y is a radical of formula Alk$^1$-NR$^5$R$^6$ then Z is selected from the group consisting of COOR$^{10}$, Alk$^4$-COOR$^{10}$ and Alk$^2$-OCOR$^{11}$ in the presence of an acid catalyst to obtain the corresponding compound of formula IV

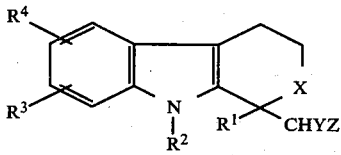

(IV)

in which R$^1$, R$^2$, R$^3$, R$^4$, X, Y and Z are as defined herein.

The conditions of the above condensation can also be used to prepare the compounds of formula I. By condensing the compound of formula II in which R$^2$, R$^3$, R$^4$ and X are as defined herein with the compound of formula III in which R$^1$ is as defined herein; Y is a radical of formula Alk$^1$-NR$^5$R$^6$ wherein Alk$^1$, R$^5$ and R$^6$ are as defined herein; and Z is a radical of formula Alk$^2$-OR$^7$ wherein Alk$^2$ and R$^7$ are as defined herein in the presence of an acid catalyst, the corresponding compound of formula I in which R$^1$, R$^2$, R$^3$, R$^4$, R$^5$, R$^6$, R$^7$, Alk$^1$ and Alk$^2$ are as defined herein is obtained. At this point, for convenience and clarity, the latter compounds of formula I will be included in the description of the preparation of the compounds of formula IV.

Thereafter the appropriate compound of formula IV is converted to the desired pyrano[3,4-]indole or thiopyrano[3,4-b]indole of formula I according to the processes described hereinafter.

In practicing the condensation (II+III→IV) a solvent is used generally as a reaction medium. Any solvent inert to the reaction conditions can be used. Suitable solvents include aromatic hydrocarbon, for example benzene, or toluene, ethers and cyclic ethers, for example diethyl ether, dioxane, or tetrahydrofuran, halogenated hydrocarbons, for example methylene dichloride, or carbon tetrachloride and the like. Benzene and tetrahydrofuran are especially convenient and practical for this use. A variety of suitable acid catalysts can be used for this condensation, for example, the type of catalyst used in a Friedel-Crafts reaction, i.e. p-toluenesulfonic acid, aluminum chloride, phosphorus pentoxide, boron trifluoride, zinc chloride, hydrochloric acid, perchloric acid, trifluoroacetic acid, sulfuric acid and the like. p-Toluenesulfonic acid, aluminum chloride, boron trifluoride and phosphorus pentoxide are included among the preferred acid catalysts. The amount of acid catalyst used is not especially critical and can range from 0.01 molar equivalents to 100 molar equivalents; however, a range of from 0.1 to 10 molar equivalents is generally preferred; however, note that the amount of acid catalyst should be in excess with respect to the basic nitrogens present in the starting material of compound III when Y is Alk$^1$-NR$^5$R$^6$. The time of the reaction may range from 10 minutes to 60 hours, with the preferred range being from one-half to 24 hours. The temperature of the reaction can range from 20° C. to the boiling point of the reaction mixture. Preferred temperature ranges include 20° to 120° C.

A more detailed description of the preparation of the above intermediate compounds of formula IV and a description of their subsequent conversion to pyranoindole and thiopyranoindole derivatives of formula I are disclosed below. For convenience these descriptions are categorized into sections according to the group selected for Y for the intermediate.

a. Preparation and conversion of Intermediates of formula IV in which Y is COOR$^8$ or Alk$^3$-COOR$^8$ Intermediates of formula IV in which R$^1$, R$^2$, R$^3$ and R$^4$ are as described herein; Y is COOR$^8$ or Alk$^3$-COOR$^8$ wherein Alk$^3$ and R$^8$ are as described herein; and Z is COOR$^{10}$, Alk$^4$-COOR$^{10}$ wherein Alk$^4$ and R$^{10}$ are as described herein, Alk$^2$-O-COR$^{11}$ wherein Alk$^2$ and R$^{11}$ are as described herein or Alk$^2$-OR$^7$ wherein Alk$^2$ and R$^7$ are as defined herein are readily obtained by the condensation (II+III→IV) by using ketoacids or ketoesters of formula III

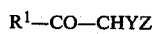 (III)

in which R$^1$ and Z are as defined herein and Y is COOR$^8$ or Alk$^1$-COOR$^8$ together with the starting material of formula II. A comprehensive review on the properties and preparation of the latter ketoacids and ketoesters of formula III can be found in "Rodd's Chemistry of the Carbon Compounds" S. Coffey, ed., Vol Id, 2nd ed., Elsevier Publishing Co., Amsterdam, 1965, pp 226-274.

Generally comparable yields of product are when either the ketoacid or the corresponding ketoester is used. However, in the case where it is desired to prepare an acid compound of formula IV in which Y is COOR$^8$ wherein R$^8$ is hydrogen, or Alk$^3$-COOR$^8$ wherein Alk$^3$ is as defined herein and R$^8$ is hydrogen (i.e. acid intermediates of formula IV), it is preferable to first condense the appropriate β-ketoester of formula III rather than the corresponding β-ketoacid and then hydrolyze the resulting ester product to give the desired acid compound.

Moreover, in the general practise of this invention it is often more convenient to prepare the acid compounds of formula IV by using the ketoester instead of the ketoacid in this process and then hydrolyze the resulting ester product to the desired acid, the reason being simply that the ketoesters are generally more readily available either commercially or by synthesis.

The hydrolysis of compounds of formula IV in which Y is COOR$^8$ wherein R$^8$ is lower alkyl, or Alk$^3$-COOR$^8$ wherein Alk$^3$ is as defined herein and R$^8$ is lower alkyl, i.e. ester intermediates of formula IV, to their corresponding acids of formula II is readily effected by treatment with a suitable alkali, for example, potassium hydroxide or sodium carbonate, in aqueous methanol or aqueous ethanol or by treatment with lithium iodide in a suitable organic solvent, for example, collidine, see L. F. Fieser and M. Fieser, "Reagents for Organic Synthesis", John Wiley and Sons, Inc., New York, 1967, pp. 615-617.

The latter hydrolysis will also hydrolyze the ester groups represented by Z in the intermediate of formula IV. Therefore, when Z is the group COOR$^{10}$ wherein R$^{10}$ is lower alkyl, or Alk$^4$-COOR$^{10}$ wherein Alk$^4$ is as defined herein and R$^{10}$ is lower alkyl, the corresponding acid (i.e. Z is COOR$^{10}$ wherein R$^{10}$ is hydrogen, or Alk$^4$COOR$^{10}$ wherein R$^{10}$ is hydrogen) will be obtained. Also, when Z represents the group Alk$^2$-OCOR$^{11}$ wherein Alk$^2$ and R$^{11}$ are as defined herein, the corresponding alcohol (i.e. Z is $Alk^2$-$OR^7$ wherein $R^7$ is hydrogen) will be obtained.

Thereafter these intermediate acids and esters of formula IV are converted to compounds of formula I in which $R^1$, $R^2$, $R^3$, $R^4$, $R^5$, $R^6$, $R^7$, X, $Alk^1$ and $Alk^2$ are as defined herein. This conversion is accomplished by amidation, reduction and if desired alkylation of the indolic nitrogen, primary amines, secondary amines and/or alcohol. The order of these steps is not critical. However, we have found the following sequence of these steps to be both convenient and practical.

In the case where the acid intermediate of formula IV is employed, said acid is activated (i.e. as the mixed anhydride, activated ester, etc) and subjected to amidation. A convenient method of amidation is to react the acid intermediate with a lower alkyl chloroformate, preferably ethyl chloroformate, in the presence of triethylamine, affording the corresponding mixed anhydride, which is converted by treatment with the appropriate amine of formula $HNR^5R^6$ in which $R^5$ and $R^6$ are as defined in the first instance, for example, ammonia, methylamine or dimethylamine, to yield the corresponding amide of formula IV in which Y is $CONR^5R^6$ or $Alk^3CONR^5R^6$ in which $Alk^3$, $R^5$ and $R^6$ are as described herein.

Alternatively, the latter amides are also obtained by treating the ester intermediates of formula IV with the appropriate amine according to known amidation methods, for example, see A. L. F. Beckwith in "The Chemistry of Amides", J. Zalicky, Ed., Interscience Publishers, New York, 1970, pp. 96–105.

In some cases, the above amidation steps must be conducted carefully so that excessive amounts of the ester or acid represented by the Z group are not converted to the amide. Usually, the use of about one to two molar equivalents of the amidation reagent and careful monitoring of the reaction will avoid this problem.

Secondly, the amides so obtained are reduced with a suitable complex metal hydride to yield the desired pyranoindoles and thiopyranoindoles. Examples of suitable complex metal hydrides are lithium aluminum hydride, lithium aluminum hydride-aluminum chloride, aluminum hydride-aluminum chloride, diborane, diisobutylaluminum hydride, borane methyl sulfide and sodium borohydride-aluminum chloride. Lithium aluminum hydride or diisobutylaluminum hydride is preferred. Preferred inert solvents for use with the complex metal hydrides are the non-hydroxylic solvents, for example, diethyl ether, dioxane, tetrahydrofuran, 1,2-dimethoxyethane and the like. The choice of solvent will depend up solubility of reactants and temperature required for reduction. Usually the reduction is conducted at 0° to 100° C., preferably 30° to 70° C. for one to ten hours. The preferred amount of complex metal hyride is in the range of two to ten molar equivalents.

It must be remembered that when doing the latter reduction a corresponding amount of the reducing agent must be added in order to reduce the esters represented by Z, i.e. Z is $COOR^{10}$, $Alk^4$-$COOR^{10}$ or $Alk^2$-$OCOR^{11}$. In this manner, the latter esters are reduced to $CH_2OH$, $Alk^4$-$CH_2$-OH and $Alk^2$-OH, respectively (i.e., to obtain the corresponding compound of formula I).

If it is desired to prepare the compounds of formula I of the above group in which $R^1$, $R^3$, $R^4$, $R^5$, $R^6$, $R^7$, X and $Alk^2$ are as defined herein, $R^2$ is lower alkyl and $Alk^1$ is $CH_2$ or $Alk^3$-$CH_2$, the acid or ester intermediate of formula IV in which $R^2$ is hydrogen is first subjected to N-alkylation by treatment with a molar excess of the appropriate lower alkyl halide in an inert solvent in the presence of an inorganic proton acceptor. Suitable inert solvents include tetrahydrofuran, benzene, toluene and dimethylformamide. Suitable proton acceptors include sodium hydride and alkali metal carbonates. Preferred conditions for effecting this N-alkylation include the use of sodium hydride as a proton acceptor and tetrahydrofuran as an inert solvent. Although the optimum temperature and reaction time will vary depending on the reactants employed, the reaction is generally performed at the boiling point of the reaction mixture for a period of 30 minutes to 48 hours.

The latter alkylation will also alkylate the compound of formula IV in which Z is $Alk^2$-$OR^7$ wherein $R^7$ is hydrogen to obtain the corresponding compound of formula IV in which Z is $Alk^2$-$OR^7$ wherein $R^7$ is lower alkyl. However, if the latter O alkylation is not desired, the alcohol is protected prior to alkylation. The alcohol is conveniently and preferably protected as the acetate. Usually, this acetylation is achieved by reacting the appropriate compound of formula IV with a molar excess of acetic anhydride at 100° to 139° C. for one to ten hours. The acetate group is easily removed at a later step by reduction with a complex metal hydride in the same manner as described above or by alkaline hydrolysis with an aqueous and/or alcoholic solution of sodium or potassium hydroxide.

In this manner, the corresponding N-alkylated derivatives of the above acid and ester derivatives of formula IV are obtained. Thereafter these derivatives are subjected to the amidation and reduction steps according to the conditions described hereinabove in this section, to afford the desired compounds of formula I in which $R^2$ is lower alkyl.

Although the above sequence of steps for the conversion of the acid and ester intermediates of formula IV to the above desired pyranoindoles is convenient and efficacious, a change in the order of the steps whereby the amides of formula IV are reacted with the appropriate lower alkyl halide according to the alkylation conditions described above, followed by reduction with a complex metal hydride, as described above, also affords the above desired compounds of formula I, in which $R^2$ and/or $R^7$ is lower alkyl.

Furthermore, another change in the order of the steps for preparing the latter compounds of formula I is realized by alkylation, as described above, of the corresponding compounds of formula I in which $R^2$ and/or $R^7$ is hydrogen, described above. In this case when the starting material employed is a pyranoindole or thiopyranoindole of formula I in which $Alk^1$ is $CH_2$ or $Alk^3$-$CH_2$ wherein $Alk^3$ is as defined herein, $R^5$ is hydrogen and $R^6$ is hydrogen or lower alkyl, i.e., a primary or secondary amine function is present in the molecule in addition to the indolic nitrogen, it is expedient to use only one molar equivalent of the appropriate organic halide to avoid alkylation of the primary or secondary amine if so desired. In addition, if desired, the alcohol (i.e. $R^7$ is hydrogen) can be protected as the acetate in the same manner as described above to avoid alkylation of the alcohol.

The primary amines of formula I (i.e. $R^5$ and $R^6$ are hydrogen) can also be N-alkylated directly without alkylating the indole nitrogen or the alcohol (i.e. $R^2$ and $R^7$ are hydrogen). This N-alkylation is accomplished by reacting the latter primary amine of formula I with one molar equivalent of a lower alkyl chloride, bromide or iodine in an inert organic solvent, preferably methanol, at 15° to 30° C. for one to four days to obtain the corresponding secondary amine compound of formula I in which $R^5$ is lower alkyl, and $R^2$, $R^6$ and $R^7$ are hydrogen. The use of two or more equivalents of the alkylating agent will result in the formation of the corresponding tertiary amine compound of formula I in which $R^5$ and $R^6$ are lower alkyl, and $R^2$ and $R^7$ are hydrogen. Furthermore, such secondary amine compounds are converted to their corresponding tertiary amine compounds by this N-alkylation procedure.

Another method for N-alkylating the primary amines of formula I without alkylating the indole nitrogen or the alcohol is also available. For this N-alkylation, the primary amine of formula I is reacted with one molar equivalent of a ketone or aldehyde in the presence of hydrogen chloride in an anhydrous solvent, preferably methanol and/or ethanol at 20° to 30° C. for 15 min to 5 hr to obtain a solution containing the corresponding imine. This imine in the solution is subsequently reduced with a molar excess of sodium cyanoborohydride to obtain the corresponding secondary amine of formula I in which $R^5$ is lower alkyl, and $R^2$, $R^6$ and $R^7$ are hydrogen. If desired the latter compound can be further N-alkylated in the same manner with the ketone or aldehyde and followed by reduction with sodium cyanoborohydride to obtain the corresponding tertiary amine of formula I in which $R^5$ and $R^6$ are lower alkyl and $R^2$ and $R^7$ are hydrogen.

Another aspect of the present intermediates of formula IV relates to their conversion to compounds of formula I in which $R^1$, $R^2$, $R^3$, $R^4$, $R^7$, X and $Alk^2$ are as defined herein and $Alk^1$ is $CH_2$ or $Alk^3$-$CH_2$ wherein $Alk^3$ is as defined herein $R^5$ is hydrogen and $R^6$ is lower alkyl, i.e. secondary amines. When it is desired to prepare the latter compounds a modification involving the protection of the secondary amine with a benzyl group or other suitable protecting group is especially convenient, see J. F. W. McOmie in "Advances in Organic Chemistry", Vol. 3, R. A. Raphael, et al., Interscience Publishers, New York, 1963, pp. 191–294. For example, the appropriate aforementioned acid or ester intermediate of formula IV is reacted with an amine of formula $HNR^6R^{12}$ in which $R^6$ is lower alkyl and $R^{12}$ is benzyl according to the amidation step described above. The resulting amide is alkylated on the indolic nitrogen and/or on the alcohol, if desired, and then reduced with a complex metal hydride according to the above procedures. Thereafter the benzyl group is removed by hydrogenolysis in the presence of a catalyst, preferably 10% palladium on carbon, to afford the desired secondary amine compounds of formula I.

Still another modification relates to a more general reduction of the above amides of formula IV in which Y is $CONR^5R^6$ or $Alk^3$-$CONR^5R^6$ wherein $Alk^3$, $R^5$ and $R^6$ are as defined herein. In other words this modification is applicable to the reduction of tertiary, secondary and primary amides, described herein, and is a preferred modification for the reduction of the latter two. In practising this modification, the aforementioned amide of formula IV is treated with triethyloxonium fluoroborate or dimethyl sulfate, see H. Bredereck et al. Chem. Ber., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride, similar to the reduction described previously for the amides, yields the corresponding compounds of formula I. Alternatively, the above fluoroborate or methyl sulfate salt derived from a secondary or primary amide is decomposed by base treatment, for example, with 10% sodium hydroxide or triethylamine, to give the corresponding iminoether which is then reduced in a like manner to the desired compound of formula I.

In some cases the reduction of the primary amide of formula IV proceeds only with difficulty and/or in low yields to the corresponding primary amine of formula I. A useful alternative method of obtaining the primary amine of formula I from the corresponding primary amide of formula IV in which Y is $Alk^3$-$CONR^5R^6$ or $CONR^5R^6$ involves the following steps: The first step involves protection of the alcohol function (i.e. $R^7$ is hydrogen), if it is present, in the amide of formula IV. This protection is easily achieved by acetylating the alcohol-amide of formula IV with a molar excess of acetic anhydride and pyridine at room temperature for 15 to 30 hours to give the corresponding primary amide, O-acetate. The next step involves the conversion of the primary amide to the corresponding nitrile. In this step, the primary amide is reacted with one to two molar equivalents of p-toluenesulfonyl chloride in pyridine at 20° to 70° C. for one to six hours and the nitrile is isolated. Finally, the latter nitrile is reduced with a complex metal hydride, preferably lithium aluminum hydride, in the same manner as described above to obtain the corresponding primary amine of formula I (i.e. $Alk^1$ is $CH_2$ or $Alk^3$-$CH_2$, and $R^5$ and $R^6$ are hydrogen). This reduction also will remove the acetate protection of the alcohol, so that the alcohol (i.e. $R^7$ is hydrogen) will be obtained.

When it is desired to prepare the tertiary amine compounds in which $R^5$ or $R^6$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which is applied to the above primary and secondary amines involves acylation with a lower alkanoic anhydride or acid halide and subsequent reduction of the resulting amide.

Furthermore, the above primary amines of formula I in which $R^5$ and $R^6$ are hydrogen can be used to prepare compounds of formula I in which $R^5$ and $R^6$ together with the nitrogen atom to which they are joined form a heterocyclic amine radical as defined in the first instance. When used in this manner the primary amines are subjected to known N-alkylation methods, for example, see method J in the report by R. B. Moffett, J. Org. Chem., 14, 862 (1949), with the appropriate $\alpha$, $\omega$-dibromides, or $\alpha$, $\omega$-dichloride, for example, tetramethylene dibromide, pentamethylene dibromide or bis(2-chloroethyl)ether to give the corresponding, desired compound of formula I in which $R^5$ and $R^6$ together with the nitrogen atom is pyrrolidino, piperidino or morpholino.

If during the above N-alkylations it is desired to protect the unsubstituted indole nitrogen ($R^2$ is hydrogen) or the alcohol group ($R^7$ is hydrogen) in the compounds of formula I, such protection for the indole nitrogen can be afforded by the use of appropriate protecting groups, for example, a benzyl group; see J. F. W. McOmie, cited above, and the protection of the alcohol group is effected by forming the acetate, as described above.

b. Preparation and conversion of intermediates of formula IV in which Y is $CONR^5R^6$ or $Alk^3\text{-}CONR^5R^6$ The intermediates of formula IV in which Y is $CONR^5R^6$ or $Alk^3\text{-}CONR^5R^6$ wherein $R^5$, $R^6$ and $Alk^3$ are as defined herein, described in the previous section, are also obtained directly by utilizing the appropriate starting materials of formula II and ketoamide of formula $R^1\text{-}CO\text{-}CHYZ$ in which $R^1$ and Z are as defined herein and Y is $CONR^5R^6$ or $Alk^3\text{-}CONR^5R^6$ wherein $Alk^3$, $R^5$ and $R^6$ are as defined herein. A comprehensive review on the properties and preparation of the latter ketoamides can be found in "Rodd's Chemistry of the Carbon Compounds", cited above.

Thereafter these amides are converted by the reduction process, and if required, alkylation processes, described in section a,, to the compounds of formula I in which $R^1$, $R^2$, $R^3$, $R^4$, $R^5$, $R^6$, $R^7$, X and $Alk^2$ are as defined herein, and $Alk^1$ is $CH_2$ or $Alk^3\text{-}CH_2$ wherein $Alk^3$ is as defined herein.

It should be noted that the compounds of formula IV in which $R^1$, $R^3$ and X are as defined herein; $R^2$ and $R^4$ are hydrogen; Y is $CONR^5R^6$ or $Alk^3\text{-}CONR^5R^6$ and Z is $CH_2CH_2\text{-}OH$, in addition to their use as intermediates for the preparation of the compounds of formula I, are useful also as intermediates for the preparation of the antidepressant agents described in the copending U.S. patent application Ser. No. 904,113, filed as of the same date, now U.S. Pat. No. 4,171,443.

c. Preparation and conversion of intermediates of formula IV in which Y is $Alk^1\text{-}NR^6\text{-}COR^9$ and Z is as defined herein Intermediates of formula IV in which Y is $Alk^1\text{-}NR^6\text{-}COR^9$ wherein $Alk^1$, $R^6$ and $R^9$ are as defined herein are readily obtained by the condensation (II+III→IV) of the starting material of formula II with an appropriate ketoamide of formula $R^1\text{-}CO\text{-}CHYZ$ in which $R^1$ and Z are as defined herein and Y is $Alk^1\text{-}NR^6\text{-}COR^9$ wherein $Alk^1$, $R^6$ and $R^9$ are as defined herein. A comprehensive review on the properties and preparation of the latter ketoamides can be found in "Rodd's Chemistry of the Carbon Compounds", cited above.

Thereafter, reduction with a complex metal hydride, and if desired alkylation as described in section a., converts the instant intermediates of formula IV to compounds of formula I in which $R^1$, $R^2$, $R^3$, $R^4$, $R^6$, $R^7$, X, $Alk^1$ and $Alk^2$ are as defined herein and $R^5$ is lower alkyl.

d. Preparation and conversion of intermediates of formula IV in which Y is $Alk^1$-halo and Z is as defined herein Intermediates of formula IV in which Y is $Alk^1$-halo wherein $Alk^1$ is as defined herein and halo is chloro, bromo or iodo, and Z is as defined herein are obtained when a starting material of formula II is condensed with a haloketone of formula $R^1\text{-}CO\text{-}CHYZ$ in which $R^1$ and Z are as defined herein and Y is $Alk^1$-halo in the presence of a suitable acid catalyst according to the conditions described above for the condensation (II+III→IV).

Thereafter these intermediates of formula IV are treated with a two molar excess of an amine of formula $HNR^5R^6$ in which $R^5$ and $R^6$ are as defined herein, and if required reduction of the ester or hydrolysis when Z is $Alk^2\text{-}OCOR^{11}$, represented by the group Z, in the same manner as described above, to yield the corresponding compound of formula I in which $R^1$, $R^2$, $R^3$, $R^4$, $R^5$, $R^6$, $R^7$, X, $Alk^1$ and $Alk^2$ are as defined herein. Preferred conditions for the reduction include the use of a suitable inert solvent, for example, tetrahydrofuran, temperatures ranging from 40°–100° C. or at the boiling point of the reaction mixture and a reaction time of from eight to 24 hours.

If desired the latter pyranoindoles and thiopyranoindoles of formula I in which $R^2$, $R^5$, $R^6$ and/or $R^7$ is hydrogen can be alkylated according to the methods described for the alkylation of the pyranoindoles and thiopyranoindoles in section a.

e. Preparation and conversion of intermediates of formula IV in which Y is $Alk^1\text{-}NO_2$ and Z is as defined herein Intermediates of formula IV in which Y is $Alk^1\text{-}NO_2$ wherein $Alk^1$ is as defined herein and Z is as defined herein, are obtained by the condensation (II+III→IV) when the starting materials of formula II and appropriate nitroketone of formula $R^1\text{-}CO\text{-}CHYZ$ in which $R^1$ and Z are as defined herein and Y is $Alk^1\text{-}NO_2$ is employed therein in the presence of a suitable acid catalyst. In this case trifluoroacetic acid is the preferred acid catalyst.

Thereafter, the latter intermediate of formula IV is reduced with a complex metal hydride, preferably lithium aluminum hydride, to afford the corresponding compound of formula I in which $R^1$, $R^2$, $R^3$, $R^4$, $R^7$, X, $Alk^1$ and $Alk^2$ are as defined herein and $R^5$ and $R^6$ are hydrogen.

If desired the latter primary amine compound of formula I in which $R^2$, $R^5$, $R^6$ and/or $R^7$ is hydrogen can be alkylated in the manner as described above in section a. to give the corresponding compound of formula I in which $R^2$, $R^5$, $R^6$ and/or $R^7$ is as defined herein.

f. Preparation of compounds of formula IV in which Y is $Alk^1\text{-}NR^5R^6$ and Z is as defined herein The above described starting materials of formula II are condensed in the presence of an acid catalyst with an aminoketone of formula $R^1\text{-}CO\text{-}CHYZ$ in which $R^1$ and Z are as defined herein and Y is $Alk^1\text{-}NR^5R^6$ wherein $Alk^1$, $R^5$ and $R^6$ are as defined herein, and, if required, reduction of the ester represented by the group Z, or hydrolysis when Z is $Alk^2\text{-}OCOR^{11}$, in the same manner as described above, to give the corresponding compound of formula I.

In practising this present condensation it is generally advantageous to utilize substantially equimolar amounts of the starting material of formula II and the aminoketone of formula III in the presence of an acid catalyst. In this particular condensation the amount of the aforementioned acid catalyst to employ ranges generally from about 1.01 to 100 molar equivalents with respect to the amount of aminoketone reactant, a range of from 1.05 to 10 molar equivalents being preferred. Optionally, one may employ the acid addition salts of the aforementioned aminoketone of formula III, for example the hydrochloride or the sulfate salt. In this case the amount of acid catalyst may range from 0.01 to 100 molar equivalents, preferably 0.1 to 10 molar equivalents. Boron trifluoride is a preferred acid catalyst for the present condensation. The reaction can be performed conveniently and advantageously without a solvent, although a high boiling solvent, for example, toluene, xylene or isobutyl ether, may be used. When the solvent is omitted, it is desirable to heat the reactants to a melt and stir the melt in an inert atmosphere, for example, nitrogen or helium. Reaction time and temperature depend on the particular reactants employed and may be varied. The most convenient reaction time is from one-half to 48 hours, preferably one-half to four hours, and reaction temperatures from 20° to 200° C., preferably 60° to 140° C. The reaction in each individual case is performed preferably at the lowest temperature at which the reaction proceeds smoothly and expeditiously with a minimum of decomposition.

The first step in another embodiment for the preparation of the compound of formula I in which $R^1$, $R^2$, $R^3$, $R^4$, $R^5$, $R^6$, $R^7$, X, $Alk^2$ are as defined herein and $Alk^1$ is $CH_2$ or $Alk^3$-$CH_2$ wherein $Alk^3$ is as defined herein is the condensation of the compound of formula II with an appropriate lower alkanoyl-lactone of formula V

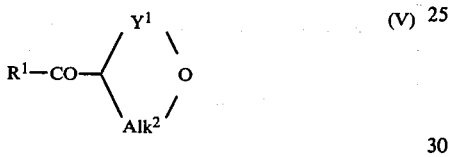

in which $R^1$ and $Alk^2$ are as defined herein and $Y^1$ is CO or $Alk^3$-CO wherein $Alk^3$ is as defined herein, in the same manner as described above for the condensation II+III→IV, to obtain the corresponding compound of formula VI

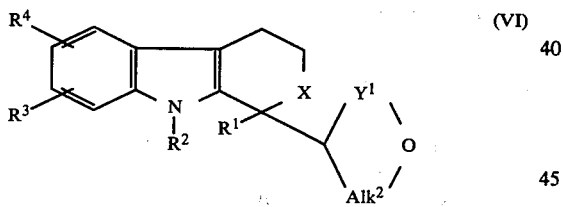

in which $R^1$, $R^2$, $R^3$, $R^4$, X, $Alk^2$ and $Y^1$ are as defined herein.

The lower alkanoyl-lactones of formula V are either known, for example, a number of 3-(lower alkanoyl)-dihydro-2(3H)-furanones are described by M. W. Wagle and T. B. Pause, Proc. Indian Acad. Sci. Sect. A, 68, 277 (1968), or they are prepared by known methods, for instance, see "Rodd's Chemistry of the Carbon Compounds", cited above, pp. 299-309 and "Rodd's Chemistry of the Carbon Compounds", M. F. Ansell, ed. Supplement to Vol Ic and Id, Elsevier Publishing Co., Amsterdam, 1973, pp. 99-113.

Subsequently, the compound of formula VI is reacted with 20 to 40 molar equivalents of an amine of formula $HNR^5R^6$ in which $R^5$ and $R^6$ are as defined herein in an inert organic solvent, preferably methanol, tetrahydrofuran or dioxane, to obtain the corresponding amide of formula IVa

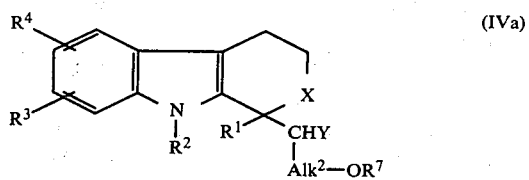

in which $R^1$, $R^2$, $R^3$, $R^4$, X and $Alk^2$ are as defined herein, $R^7$ is hydrogen and Y is a radical of formula $Alk^3$-$CONR^5R^6$ wherein $Alk^3$, $R^5$ and $R^6$ are as defined herein, or $CONR^5R^6$ wherein $R^5$ and $R^6$ are as defined herein. This reaction usually requires a temperature of 45° to 100° C. for 10 to 30 hours. The amide of formula IVa corresponds to the compound of formula IV in which Y is $CONR^5R^6$ or $Alk^3$-$CONR^5R^6$ and Z is $Alk^2$-$OR^7$ wherein $R^7$ is hydrogen.

If desired, the amide of formula IVa in which $R^7$ is hydrogen, and $R^2$, $R^5$ and/or $R^6$ is hydrogen can be alkylated in the same manner as described above to obtain the corresponding compound of formula IVa in which $R^2$, $R^5$, $R^6$ and/or $R^7$ is lower alkyl.

The amides of formula IVa are reduced with a complex metal hydride, in the same manner as described above, to obtain the corresponding compound of formula I in which $R^1$, $R^2$, $R^3$, $R^4$, $R^5$, $R^6$, $R^7$, X and $Alk^2$ are as defined herein and $Alk^1$ is $CH_2$ or $Alk^3$-$CH_2$ wherein $Alk^3$ is as defined herein.

If desired, the latter compound of formula I in which $R^2$, $R^5$, $R^6$ and/or $R^7$ is hydrogen can be alkylated, in the same manner as described above, to obtain the corresponding compound of formula I in which $R^2$, $R^3$, $R^6$ and/or $R^7$ is lower alkyl.

A particularly useful process for preparing a preferred group of compounds of formula I is illustrated by reaction scheme 1.

Reaction scheme 1

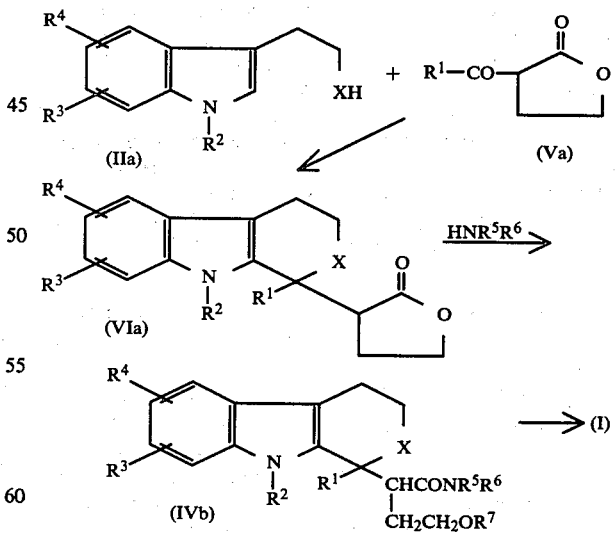

Note, in reaction scheme 1 the compounds of formula IIa, Va, VIa and IVb are included within the scope of the definitions of the compounds of formula II, V, VI and IVa respectively.

With reference to reaction scheme 1, the compound of formula IIa in which $R^2$ is hydrogen or lower alkyl, $R^3$ and $R^4$ are hydrogen and X is oxa or thia is condensed with a 3-(lower alkanoyl)dihydro-2(3H)furanone of formula Va in which $R^1$ is as defined herein, in the same manner as described above for the condensation "II+III→IV", to obtain the corresponding compound of formula VIa in which $R^1$, $R^2$, $R^3$, $R^4$ and X are as defined immediately above. Subsequent reaction of the compound of formula VIa with 10 to 40 molar equivalents of an amine of formula $HNR^5R^6$ in which $R^5$ is lower alkyl and $R^6$ is hydrogen or lower alkyl in an inert organic solvent, preferably methanol, tetrahydrofuran or dioxane, gives the corresponding alcohol of formula IVb in which $R^1$, $R^2$, $R^3$, $R^4$, $R^5$, $R^6$ and X are as defined immediately above and $R^7$ is hydrogen. This amidation usually requires a temperature of 45° to 100° C. for 10 to 30 hours. If desired, the latter compound of formula IVb in which $R^7$ is hydrogen, and $R^2$ and/or $R^6$ is hydrogen can be alkylated in the same manner as described above to obtain the corresponding compound of formula IVb in which $R^2$, $R^6$ and/or $R^7$ is lower alkyl. Reduction of the compound of formula IVb with a complex metal hydride, in the same manner as described above, gives the corresponding compound of formula I in which $R^1$ and $R^5$ each is lower alkyl; $R^2$, $R^6$ and $R^7$ each is hydrogen or lower alkyl; $R^3$ and $R^4$ are hydrogen; X is oxa or thia; $Alk^1$ is $CH_2$; and $Alk^2$ is $(CH_2)_2$. Again, if desired, the latter compound of formula I in which $R^2$, $R^6$ and/or $R^7$ is hydrogen can be alkylated in the same manner as described above to obtain the corresponding compound of formula I in which $R^2$, $R^6$ and/or $R^7$ is lower alkyl.

Finally, it is the intention to cover all changes and modifications of the embodiment of the invention herein chosen for the purpose of disclosure which are within the scope and spirit of this invention. Such changes and modification include those variations which depend on well known interconversions of amines, amides, acids and esters or alternation of the order of the steps in the processes disclosed herein.

The following examples illustrate further this invention.

EXAMPLE 1

Dihydro-3-(1,3,4,9-tetrahydro-1-methylpyrano[3,4-b]indol-1-yl)-2(3H)-furanone (VIa; $R^1$=$CH_3$: $R^2$, $R^3$ and $R^4$=H, and X=O)

p-Toluenesulfonic acid (0.50 g) is added to a solution of 3-acetyldihydro-2(3H)-furanone (25.6 g, 0.2 mole), tryptophol (32.2 g, 0.2 mole) and benzene (700 ml). The flask is equipped with a water separator and a condenser. The mixture is stirred at reflux for one hr. More p-toluenesulfonic acid (0.50 g) is added and the solution is refluxed for 18 hr.

The dark solution is cooled and stirred in presence of silica gel (100 g) for 5 min. The mixture is filtered on diatomaceous earth and charcoal. The silica gel is washed with diethyl ether and the filtrates are evaporated to afford an oil (37 g) which is a mixture of two diasteroisomers of the title compound. If desired, the latter oil can be crystallized from methanol to obtain crystals (17 g) of isomer A of the title compound, mp 162°–164° C. The mother liquor of this crystallization is evaporated to obtain a residue (20 g) containing mainly isomer B of the title compound.

EXAMPLE 2

1,3,4,9-Tetrahydro-α-(2-hydroxyethyl)-N,N,1-trimethylpyrano[3,4-b]indole-1-acetamide (IVb; $R^1$, $R^5$ and $R^6$=$CH_3$; $R^2$, $R^3$, $R^4$ and $R^7$=H, and X=O)

A solution of the oil containing the two diasteriomers of dihydro-3-(1,3,4,9-tetrahydro-1-methylpyrano[3,4-b]indol-1-yl)-2(3H)-furanone (described in Example 1, 15 g, 0.055 mole) in tetrahydrofuran (200 ml) and an aqueous solution of dimethylamine (40%, 200 ml) is refluxed for 24 hr. Aqueous sodium chloride solution is added and the solution is extracted with diethyl ether. The organic extract is dried and evaporated to afford an oil consisting of two diasteriomeric amides of the title compound. The oil is subjected to chromatography on silica gel using acetone-benzene (1:3). The eluates are evaporated and crystallized from benzenehexane to obtain isomer A of the title compound as crystals (4.5 g), mp 158°–160° C. Further elution of the column with acetone-benzene (1:1), evaporation of the eluates and crystallization of the residue from benzene-hexane gives isomer B of the title compound as crystals (1.5 g), mp 159°–162° C.

EXAMPLE 3

γ-[(Dimethylamino)methyl]-1,3,4,9-tetrahydro-1-methylpyrano[3,4-b]indole-1-propanol (I; $R^1$, $R^5$ and $R^6$=$CH_3$; $R^2$, $R^3$, $R^4$ and $R^7$=H; X=O; $Alk^1$=$CH_2$; and $Alk^2$=$CH_2CH_2$)

A solution of 1,3,4,9-tetrahydro-α-(2-hydroxyethyl)-N,N,1-trimethylpyrano-[3,4-b]indole-1-acetamide, isomer A, (described in Example 2, 10.0 g, 0.0316 mole) in dry tetrahydrofuran (100 ml) is added dropwise under nitrogen to a mechanically stirred suspension of lithium aluminium hydride (3.0 g, 0.077 mole) in dry tetrahydrofuran (100 ml) cooled to 0° C. The mixture is refluxed for 3 hr and cooled in an ice-water bath. A solution of water-tetrahydrofuran (1:1) is added dropwise to destroy the excess hydride. The mixture is filtered and the filtrate is evaporated. The residue is dissolved in diethyl ether and the solution is washed with a saturated sodium chloride solution, dried over magnesium sulfate and evaporated. The residue is crystallized from dichloromethane-diethyl ether to give crystals (9.5 g) of isomer A of the title compound, mp 201°–204° C. and nmr (DMSO)δ 1.51(s), 2.01(s), 3.55(t), 3.90(m), 5.46(s), 7.23(m) and 10.74. To a solution of the latter compound (3.02 g) in diethyl ether (200 ml), maleic acid (1.16 g) in acetone (6 ml) is added dropwise. The precipitate is collected and crystallized from dichloromethane-benzene-diethyl ether to obtain crystals of the maleate salt, mp 88°–90° C., of the title compound.

In the same manner but replacing isomer A of the starting material with an equivalent amount of isomer B (described in Example 2), isomer B of the title compound, crystallized from methanol-diethyl ether, is obtained, mp 186°–189° C.

In the same manner but replacing 3-acetyldihydro-2(3H)-furanone in Example 1 with an equivalent amount of the following compounds of formula V: 4-propionyldihydro-2(3H)-furanone, 3-acetyl-4-methyldihydro-2(3H)-furanone, 4-pentionyldihydro-2(3H)-furanone, 4-acetyl-tetrahydro-2H-pyran-2-one, 4-propanoyl-6-methyl-tetrahydro-2H-pyran-2-one, 5-butanoyl-oxacyclooctan-2-one, 4-acetyl-6-ethyl-oxacyclooctan-2-one, 7-propionyl-4-methyl-oxacyclodecan-2-one or 8-acetyloxacyclotetradecan-2-one, and following the procedure of Examples 1, 2 and 3, the following compounds of formula I are obtained, respectively: β-[2-(dimethylamino)ethyl]-1,3,4,9-tetrahydro-1-ethylpyrano[3,4-b]indole-1-ethanol, β-methyl-γ-[(dimethylamino)methyl]-1,3,4,9-tetrahydro-1-methylpyrano[3,4-b]indole-1-propanol, β-[2-(dimethylamino)ethyl]-1,3,4,9-tetrahydro-1-butylpyrano[3,4-b]indole-1-ethanol, γ-[2-(dimethylamino)ethyl]-1,3,4,9-tetrahydro-1-methylpyrano[3,4-b]indole-1-propanol, α-methyl-γ-[2-(dimethylamino)ethyl]-1,3,4,9-tetrahydro-1-ethylpyrano[3,4-b]indole-1-propanol, δ-[3-(dimethylamino)propyl]-1,3,4,9-tetrahydro-1-propylpyrano-[3,4-b]indole-1-butanol, γ-ethyl-ε-[2-(dimethylamino)ethyl]-1,3,4,9-tetrahydro-1-methylpyrano[3,4-b]indole-1-pentanol, δ-[5-(dimethylamino)-3-methylpentyl]-1,3,4,9-tetrahydro-1-ethylpyrano[3,4-b]indole-1-butanol and η-[6-(dimethylamino)hexyl]-1,3,4,9-tetrahydro-1-methylpyrano[3,4-b]indole-1-heptanol.

By following the procedure of Examples 1, 2 and 3 using the appropriate starting materials of formulae II and Va and amine of formula $HNR^5R^6$, other compounds of formula I are obtained. Examples of the latter compounds of formula I are listed as products in tables 1 and 2 together with the appropriate starting materials of formulae II and Va and amine of formula $HNR^5R^6$ used for the preparation of the compound of formula I.

TABLE 1

| Ex. | Starting Material of Formula II | | | | Starting Material of Formula Va | Amine of Formula | Product:[(prefix listed below)-1,3,4,9-tetrahydropyrano[3,4-b]indole-1-propanol] |
|---|---|---|---|---|---|---|---|
| | $R^2$ | $R^3$ | $R^4$ | X | $R^1$ | $HNR^5R^6$ | Prefix |
| 4 | H | 4-Cl | H | O | $CH_3$ | $HN(CH_3)_2$ | γ-[(dimethylamino)methyl]-5-chloro-1-methyl, isomer A, mp 219-220° C. and isomer B, mp 170-171° C. |
| 5 | H | 7-$C_2H_5$ | H | O | $CH_3$ | $HN(CH_3)_2$ | γ-[(dimethylamino)methyl]-8-ethyl-1-methyl, isomer A, mp 194-194.5° C. and isomer B, mp 148-149° C. |
| 6 | H | 6-Cl | 7-$CH_3$ | O | $CH_3$ | $HN(CH_3)_2$ | γ-[(dimethylamino)methyl]-7-chloro-1,8-dimethyl, isomer A, mp 218-219° C. and isomer B, mp 194.5-196° C. |
| 7 | H | H | H | O | $C_3H_7$ | $HN(CH_3)_2$ | γ-[dimethylamino)methyl]-1-propyl, isomer A, mp 200-202° C. and isomer B, mp 200-201° C. |
| 8 | H | H | H | O | $CH_3$ | morpholine | γ-(morpholin-4-ylmethyl)-1-methyl, isomer A, mp 181-182° C. |
| 9 | H | H | H | O | $CH_3$ | pyrrolidine | γ-[(pyrrolidin-1-ylmethyl-1-methyl, isomer A, mp 193-195° C. |
| 10 | H | 5-Br | H | O | $C_2H_5$ | $HN(C_2H_5)_2$ | γ-[(dimethylamino)methyl]-6-bromo-1-ethyl |
| 11 | H | 4-$NO_2$ | 6-$C_3H_7$ | O | $C_2H_5$ | $HN(CH_3)_2$ | γ-[(dimethylamino)methyl]-1-ethyl-5-nitro-7-propyl |
| 12 | $CH_3$ | 6-$CF_3$ | H | O | $CH_3$ | $H_2NCH_3$ | γ-[(methylamino)methyl]-1,9-dimethyl-7-trifluoromethyl |
| 13 | H | 5-$CH_3$ | 7-$CH_3$ | O | $C_3H_7$ | $H_2NC_3H_7$ | γ-[(propylamino)methyl]-6,8-dimethyl-1-propyl |
| 14 | $C_2H_5$ | 4-$C_2H_5O$ | H | O | $C_5H_{11}$ | $H_2NC_2H_5$ | γ-[(ethylamino)methyl]-9-ethyl-5-ethoxy-1-pentyl |
| 15 | $C_3H_7$ | 6-$C(CH_3)_2$—$CH_3$ | H | O | $C_3H_7$ | $HN(C_4H_9)_2$ | γ-[(dibutylamino)methyl]-7-(1,1-dimethylethyl)-1,9-dipropyl |
| 16 | $CH_3$ | 6-$C_4H_9$ | H | O | $C_6H_{13}$ | $HN(CH_3)_2$ | γ-[(dimethylamino)methyl]-7-butyl-9-methyl-1-hexyl |
| 17 | H | H | H | O | $CH_2CH(CH_3)_2$ | $NH_3$ | γ-aminomethyl-1-(2-methylpropyl) |
| 18 | H | 4-$C_6H_{13}$ | H | O | $CH_3$ | $H_2NC_2H_5$ | γ-[(ethylamino)methyl]-5-hexyl-1-methyl |
| 19 | $C_5H_{11}$ | H | H | O | $CH_3$ | $HN(CH_3)$—$(C_2H_5)$ | γ-[(N-ethyl-N-methylamino)methyl]-1-methyl-9-pentyl |
| 20 | $C_2H_5$ | 4-$CH_3$ | 6-$CH_3$ | O | $C_2H_5$ | $NH_3$ | γ-aminomethyl-1,9-diethyl-5,7-dimethyl |
| 21 | H | 5-$C_3H_7O$ | H | O | $C_3H_7$ | piperidine | γ-(piperidine-1-ylmethyl)-1-propyl-6-propoxy | thyl]-1,3,4,9-tetrahydro-1-methylpyrano[3,4-b]indole-1-

TABLE 2

| Example | Starting Material of Formula II | | | | Starting Material of Formula Va | Amine of Formula | Product:[(prefix listed below)-1,3,4,9-tetrahydro-thiopyrano[3,4-b]indole-1-propanol] |
|---|---|---|---|---|---|---|---|
| | $R^2$ | $R^3$ | $R^4$ | X | $R^1$ | $HNR^5R^6$ | Prefix |
| 22 | H | H | H | S | $CH_3$ | $HN(CH_3)_2$ | γ-[(dimethylamino)methyl]-1-methyl, isomer A, mp 189-190° C. and isomer B, mp 228-230° C. |
| 23 | H | 5-$C_6H_{13}$ | H | S | $C_3H_7$ | morpholine | γ-(morpholin-1-ylmethyl)-6-hexyl-1-propyl |
| 24 | $C_4H_9$ | 4-$CH_3$ | H | S | $C_2H_5$ | $H_2NC_2H_5$ | γ-[(ethylamino)methyl]-9-butyl-1-ethyl-5-methyl |
| 25 | $CH_3$ | 6-$CH_3$ | 7-$NO_2$ | S | $CH_3$ | $H_2NCH_2CH$—$(CH_3)_2$ | γ-[[(2-methylpropyl)amino]methyl]1,7,9-trimethyl-8-nitro |
| 26 | H | 4-$C_4H_9O$ | H | S | $C_4H_9$ | $HN(C_5H_{11})_2$ | γ-[(dipentylamino)methyl]-1-butyl-5-butoxy |
| 27 | H | 7-$CF_3$ | H | S | $C_6H_{13}$ | pyrrolidine | γ-[(pyrrolidin-1-ylmethyl)-1-hexyl-8-trifluoromethyl |
| 28 | $CH_3$ | 6-Cl | 7-$CH_3$ | S | $CH_3$ | $NH_3$ | γ-aminoethyl-7-chloro-1,8,9-trimethyl |
| 29 | H | 5-Br | H | S | $CH_3$ | $HN(CH_3)$—$(C_3H_7)$ | γ-[(N-methyl-N-propylamino)methyl]-6-bromo 1-methyl |
| 30 | H | 5-$NO_2$ | 6-I | S | $C_2H_5$ | $HN(C_2H_5)_2$ | γ-[(diethylamino)methyl]-1-ethyl-7-iodo-6-nitro |
| 31 | $C_2H_5$ | 4-F | H | S | $C_3H_7$ | piperidine | γ-piperidin-1-ylmethyl-9-ethyl-5-fluoro-1-propyl |

TABLE 2-continued

| Example | Starting Material of Formula II | | | Starting Material of Formula Va | | Amine of Formula $HNR^5R^6$ | Product:[(prefix listed below)-1,3,4,9-tetrahydro-thiopyrano[3,4-b]indole-1-propanol] |
|---|---|---|---|---|---|---|---|
| | $R^2$ | $R^3$ | $R^4$ | X | $R^1$ | | Prefix |
| 32 | H | 5-CH$_3$O | 6-Cl | S | CH$_3$ | NH$_3$ | γ-aminomethyl-7-chloro-1-methyl-6-methoxy |

EXAMPLE 33

N,1-Dimethyl-α-(2-hydroxyethyl)-1,3,4,9-tetrahydropyrano[3,4-b]indole-1-acetamide (IVb; $R^1$ and $R^5$=CH$_3$; $R^2,R^3,R^4,R^6$ and $R^7$=H; and X=O)

A solution of 4,5-dihydro-3-(1,3,4,9-tetrahydro-1-methylpyrano[3,4-b]indol-1-yl)-2(3H)-furanone (described in Example 1, 20 g, 0.074 mole) in tetrahydrofuran (200 ml) and 40% aqueous methylamine (200 ml) is refluxed for 24 hr. The reaction mixture is diluted with brine and extracted with diethyl ether. The organic extracts are washed with brine, dried over magnesium sulfate and evaporated. The residue is subjected to chromatography on silica gel using acetone-benzene (1:2). The eluates are evaporated and crystallized from diethyl ether-hexane to obtain isomer A (6.9 g) of the title compound, mp 169°–171° C. The eluant for the column is changed to acetone-benzene (1:1) and the eluates are evaporated followed by trituration of the residue to obtain isomer B (7.5 g) of the title compound, mp 194°–196° C.

EXAMPLE 34

γ-[(Methylamino)methyl]-1,3,4,9-tetrahydro-1-methylpyrano[3,4-b]indole-1-propanol (I; $R^1$ and $R^5$=CH$_3$; $R^2,R^3,R^4,R^6$ and $R^7$=H; X=O, Alk$^1$=CH$_2$; and Alk$^2$=CH$_2$CH$_2$)

A solution of α-(2-hydroxyethyl)-1,3,4,9-tetrahydro-N,1-dimethylpyrano[3,4-b]indole-1-acetamide, isomer A (described in Example 33, 0.64 g, 2.12 mmole) in acetic anhydride (20 ml) is refluxed for 2.5 hr and stirred overnight at room temperature. The acetic anhydride is evaporated under reduced pressure and the residue is dissolved in chloroform. The solution is washed with a saturated sodium bicarbonate solution and brine, dried over magnesium sulfate, filtered through diatomaceous earth and charcoal, and evaporated. The residue is crystallized from benzene-hexane to obtain isomer A (0.056 g) of α-2-acetoxyethyl)-1,3,4,9-tetrahydro-N-1-dimethylpyrano[3,4-b]indole-1-acetamide, mp 162°–164° C.

To a solution of the latter compound (5.1 g, 14.7 mmole) in dry dichloromethane (65 ml), stirring at room temperature, is added in one portion triethyloxonium fluoroborate (4.0 g). The mixture is stirred at room temperature overnight. The dichloromethane solution is washed with sodium bicarbonate solution and brine, dried over magnesium sulfate and evaporated to give a residue of the imino ether. The residue is dissolved in dry tetrahydrofuran (50 ml) and the solution is added dropwise to a suspension of lithium aluminium hydride (1.71 g, 45 mmole) in dry tetrahydrofuran (75 ml). The mixture is stirred at reflux temperature for three hr and cooled in an ice bath. A solution of water-tetrahydrofuran (1:4, 20 ml) is added dropwise to destroy excess hydride. The mixture is filtered through diatomaceous earth. The filtrate is washed with brine, dried over magnesium sulfate and evaporated. The residue is crystallized from a solution of benzene and hexane. The gummy crystals are collected and triturated with a solution of benzene and hexane on a porous porcelain plate to afford the title compound as an amorphous powder (2.2 g); mp 122° C., nmr(CDCl$_3$) δ1.6(s), 2.38(s) and 7.3(m).

EXAMPLE 35

α-(2-Acetoxyethyl)-1,3,4,9-tetrahydro-N,N,1,9-tetramethylpyrano[3,4-b]indole-1-acetamide (IV; $R^1$ and $R^2$=CH$_3$, $R^3$ and $R^4$=H, X=O, Y=CON(CH$_3$)$_2$ and Z=CH$_2$CH$_2$—OCOCH$_3$)

A solution of α-(2-hydroxyethyl)-1,3,4,9-tetrahydro-N,N,1-trimethylpyrano[3,4-b]indole-1-acetamide, isomer A (described in Example 2, 30.6 g, 0.1 mole) in acetic anhydride (300 ml) is refluxed for 2.5 hr and stirred overnight at room temperature. The acetic anhydride is evaporated under reduced pressure and the residue is dissolved in benzene. Charcoal is added and the mixture is filtered. The filtrate is reduced in volume and hexane is added to obtain crystals (30.7 g), mp 142°–143° C., of α-acetoxyethyl)-1,3,4,9-tetrahydro-N,N,1-trimethylpyrano[3,4-b]indole-1-acetamide, isomer A.

A solution of the latter compound (25.0 g, 0.07 mole) in dry tetrahydrofuran (150 ml) is added dropwise to a stirred suspension of sodium hydride (57% oil dispersion, 7.0 g, 0.145 mole) in dry tetrahydrofuran (225 ml) keeping the temperature below 15° C. and the reaction mixture is stirred for 45 min. Methyl iodide (13 ml) is added dropwise and the mixture is heated to 40°–43° C. to start the reaction which proceeds on its own for a while. The mixture is refluxed for 2 hr and cooled. Water is added dropwise to destroy excess sodium hydride. Brine (200 ml) is added and the mixture is extracted with diethyl ether. The organic extract is washed with brine, dried and evaporated. The residue is chromatographed on silica gel using 2% methanol in ethyl acetate as eluant. The initial eluates are evaporated to obtain isomer A (12.8 g) of the title compound, nmr(CDCl$_3$) δ1.66(s), 2.0(s), 3.02(s), 3.15(s), 3.9(s) and 7.3(m). The latter eluates are evaporated to obtain isomer A (8.3 g) of α-(2-methoxyethyl)-1,3,4,9-tetrahydro-N,N,1,9-tetramethylpyrano[3,4-b]indole-1-acetamide, nmr(CDCl$_3$) δ1.65(s), 2.97(s), 3.15(s), 3.30(s), 3.88(s) and 7.2(m).

EXAMPLE 36

γ-[(Dimethylamino)methyl]-1,9-dimethyl-1,3,4,9-tetrahydropyrano[3,4-b]indole-1-propanol (I; $R^1,R^2,R^5$ and $R^6$=CH$_3$; $R^3,R^4$ and $R^7$=H; X=O; Alk$^1$=CH$_2$; and Alk$^2$=CH$_2$CH$_2$)

A solution of α-(2-acetoxyethyl)-1,3,4,9-tetrahydro-N,N,1,9-tetramethylpyrano[3,4-b]indole-1-acetamide (described in Example 35, 12.8 g, 0.034 mole) in dry tetrahydrofuran (200 ml) is added dropwise to a suspension of lithium aluminum hydride (4.1 g, 0.1 mole) in dry tetrahydrofuran (150 ml). The reaction mixture is refluxed for 2 hr and cooled in an ice bath and a solution of water-tetrahydrofuran (1:4) is added carefully to destroy excess hydride. The mixture is filtered through diatomaceous earth. The filtrate is washed with brine, dried over magnesium sulfate and evaporated to give an oil (10.6 g) of isomer A of the title compound, nmr(CDCl$_3$) δ1.65(s), 2.08(s), 3.75(s), 3.85(s) and 7.25(m). The latter oil is dissolved in diethyl ether and a solution of hydrogen chloride in diethyl ether is added. The precipitate is collected and crystallized from dichloromethane-diethyl ether to obtain crystals (8.5 g), mp 192°–194° C., of the hydrochloride salt of isomer A of the title compound.

EXAMPLE 37

N,N-Dimethyl-4-methoxy-2-(1,9-dimethyl-1,3,4,9-tetrahydropyrano[3,4-b]indol-1-yl)butanamine (I; R$^1$,R$^2$,R$^5$,R$^6$ and R$^7$=CH$_3$; R$^3$ and R$^4$=H; X=O; Alk$^1$=CH$_2$; and Alk$^2$=CH$_2$CH$_2$)

A solution of α-(2-methoxyethyl)-1,3,4,9-tetrahydro-N,N,1,9-tetramethylpyrano[3,4-b]indole-1-acetamide, isomer A (described in Example 35, 8.3 g, 0.024 mole) in dry tetrahydrofuran (100 ml) is added dropwise with stirring to a cooled suspension of lithium aluminum hydride (2.5 g, 0.065 mole) in dry tetrahydrofuran (150 ml). The reaction mixture is refluxed for 2 hr and cooled in ice. A solution of water-tetrahydrofuran (1:3) is added carefully to destroy excess hydride and the mixture is filtered through diatomaceous earth. The filtrate is washed with brine, dried over magnesium sulfate and evaporated. The residue is crystallized from methanol-water to give the title compound (4.97 g), mp 77°–78° C.

EXAMPLE 38

2-(1,3,4,9-Tetrahydro-1-methylpyrano[3,4-b]indole-1-yl)-glutaric Acid Diethyl Ester (IV; R$^1$=CH$_3$; R$^2$,R$^3$ and R$^4$=H; X=O; Y=CH$_2$CH$_2$—COOEt; and Z=COOEt)

A solution of tryptophol (16.12 g, 0.1 mole), diethyl 2-acetylglutarate (23.25 g, 0.1 mole) and p-toluenesulfonic acid (0.25 g) in dry benzene (275 ml) is stirred at reflux temperature overnight using a water trap. More p-toluenesulfonic acid (0.10 g) is added and reflux is continued for 6 hr at the end of which the theoretical amount of water (1.8 ml) is collected. Diatomaceous earth (ca 60 ml) and charcoal are added to the dark red mixture and a pale yellow filtrate is obtained upon filtration. Concentration of the filtrate gives a thick oil which is chromatographed on silica gel using 15% acetone in benzene as eluant. The eluates are evaporated to give the title compound as a mixture of two diastereomers (31.5 g), nmr(CDCl$_3$) δ1.20(t), 1.55(s), 2.25(m), 2.9(m), 4.2(m), 7.3(m) and 9.5(s).

EXAMPLE 39

5-(N,N-Dimethylamino)-2-(1-methyl-1,3,4,9-tetrahydropyrano[3,4-b]indol-1-yl)-5-oxopentanoic Acid Ethyl Ester (IV; R$^1$=CH$_3$; R$^2$,R$^3$ and R$^4$=H; X=O; Y=CH$_2$CH$_2$—CON(CH$_3$)$_2$ and Z=COOEt)

To a stirred solution of 2-(1,3,4,9-tetrahydro-1-methylpyrano[3,4-b]indol-1-yl)-glutaric acid diethyl ester (described in Example 38, 7.46 g, 0.02 mole) in methanol is added gaseous dimethylamine using a dry ice condenser and the solution is refluxed overnight using a water condenser. Excess dimethylamine and methanol are removed under reduced pressure and the residue is chromatographed on silica gel using 20% acetone in benzene. The appropriate eluate fractions are combined and evaporated. The residue is crystallized from benzene-hexane to obtain the title compound as crystals (3.9 g), mp 86°–88° C.

EXAMPLE 40

β-[γ-(N,N-Dimethylamino)propyl]-1-methyl-1,3,4,9-tetrahydropyrano[3,4-b]indole-1-ethanol (I; R$^1$,R$^5$ and R$^6$=CH$_3$; R$^2$,R$^3$,R$^4$ and R$^7$=H; X=O; Alk$^1$=CH$_2$CH$_2$CH$_2$; and Alk$^2$=CH$_2$)

A solution of 5-(N,N-dimethylamino)-2-(1-methyl-1,3,4,9-tetrahydropyrano[3,4-b]indol-1-yl)-5-oxopentanoic acid ethyl ester (described in Example 39, 2.28 g, 6.15 mmole) in dry tetrahydrofuran (50 ml) is added dropwise to a stirred suspension of lithium aluminium hydride (0.96 g, 20 mmole) in dry tetrahydrofuran (50 ml) at 0° C. under nitrogen. The suspension is stirred at reflux temperature for 3 hr and cooled in an ice-bath. A mixture of water-tetrahydrofuran (1:4) is added carefully to destroy excess lithium aluminium hydride. The mixture is filtered through diatomaceous earth and the filtrate is washed with brine, dried over magnesium sulfate and evaporated. The residue is crystallized from benzene to obtain the title compound as crystals (0.96 g), mp 100°–102° C.

EXAMPLE 41

γ-Aminomethyl-1-methyl-1,3,4,9-tetrahydropyrano[3,4-b]indole-1-propanol (I; R$^1$=CH$_3$; R$^2$,R$^3$,R$^4$,R$^5$,R$^6$ and R$^7$=H; X=O; Alk$^1$=CH$_2$; and Alk$^2$=CH$_2$CH$_2$)

A suspension of 4,5-dihydro-3-(1,3,4,9-tetrahydro-1-methylpyrano[3,4-b]indol-1-yl)-2(3H)-furanone (described in Example 1, 20 g, 0.073 mole) in liquid ammonia is heated at 90° C. in a pressure apparatus for three hours. The apparatus is rinsed with ethanol and the yellow solution is evaporated. The residue is crystallized from methanol to afford α-(2-hydroxyethyl)-1-methyl-1,3,4,9-tetrahydropyrano[3,4-b]indole-1-acetamide (16.15 g), mp 159°–161° C.

A solution of the latter compound (9.0 g, 0.031 mole) in acetic anhydride (150 ml) is refluxed for three hours, allowed to stand at room temperature overnight and evaporated. The residue is dissolved in chloroform. The organic solution is washed with aqueous sodium bicarbonate, brine, dried over magnesium sulfate and evaporated. The residue is chromatographed on silica gel with a mixture 20% acetone in benzene. The eluates are evaporated to give a residue (5.3 g) of α-(2-acetoxyethyl)-N-acetyl-1-methyl-1,3,4,9-tetrahydropyrano[3,4-b]indole-1-acetamide, ir(CHCl$_3$) 1700 and and 1725 cm$^{-1}$.

A solution of the latter compound (20 g, 0.07 mole) in acetic anhydride (70 ml) and pyridine (60 ml) is left in the dark at room temperature for 24 hours. The reaction mixture is evaporated and the residue is chromatographed on silica gel (650 g) using ethyl acetate. The eluates are evaporated and the residue is crystallized from benzene-hexane to afford isomer A (15.7 g) of α-(2-acetoxyethyl)-1-methyl-1,3,4,9-tetrahydropyrano[3,4-b]indole-1-acetamide, mp 141°–143° C. Further elution of the column with 5% methanol in ethyl acetate, evaporation of the eluates and crystallization of the residue from methanol-water gives isomers B (4.1 g) of the latter compound, mp 186°–188° C.

To a stirred mixture of isomer A of the latter compound (15 g, 0.045 mole) and pyridine (9.0 g, 0.15 mole) is added p-toluenesulfonyl chloride (10.0 g, 0.052 mole) at such a rate that the temperature does not exceed 70°

C. The mixture is stirred at room temperature for three hr, excess ethyl acetate is added and the resulting mixture is filtered. The filtrate is washed with water and evaporated. The residue is chromatographed through a column of silica gel using ethyl acetate-benzene (1:10). The eluates are concentrated down to 30 ml, diethyl ether is added and the crystals (12.5 g) of isomer A of 1,3,4,9-tetrahydro-α-(2-acetyloxyethyl)-1-methyl-pyrano[3,4-b]indole-1-acetonitrile, mp 115°–117° C., are collected.

A solution of the latter compound (10.0 g, 0.032 mole) in dry tetrahydrofuran (100 ml) is added dropwise to a mechanically stirred mixture of lithium aluminum hydride (5.0 g, 0.13 mole) and dry tetrahydrofuran (100 ml) under nitrogen. The reaction mixture is stirred at room temperature for one hr under nitrogen and cooled to 0° C. A solution of water-tetrahydrofuran (1:9, 100 ml) is slowly added followed by diatomaceous earth (10 g). The mixture is stirred for a few minutes and filtered through a pad of diatomaceous earth. The filtrate is concentrated to about 50 ml and ethyl acetate is added. The solution is washed with brine and extracted with 1N hydrochloric acid (100 ml). The acidic extract is basified with sodium hydroxide and the alkaline solution is extracted with ethyl acetate. The organic extract is dried, evaporated and crystallized from methanol to afford isomer A (3.8 g) of the title compound, mp 172°–174° C. The title compound is dissolved in methanol and a solution of hydrogen chloride in diethyl ether is added. The solution is allowed to crystallize and the crystals of the hydrochloric salt of isomer A of the title compound, mp 225°–228° C., are collected.

EXAMPLE 42

γ-[N-(1-Methylethyl)aminomethyl]-1-methyl-1,3,4,9-tetrahydropyrano[3,4-b]indole-1-propanol (I; $R^1$=$CH_3$; $R^2$, $R^3$, $R^4$, $R^5$ and $R^7$=H; $R^6$=$CH(CH_3)_2$; X=O, $Alk^1$=$CH_2$; and $Alk^2$=$CH_2CH_2$)

To a solution of γ-aminomethyl-1-methyl-1,3,4,9-tetrahydropyrano[3,4-b]indole-1-propanol (described in Example 41, 2.88 g, 0.014 mole) in absolute methanol (1 ml) is added 5 N hydrogen chloride in ethanol (0.5 ml) followed by anhydrous acetone (0.58 g, 0.01 mole) and the reaction mixture is stirred for 0.5 hr. Sodium cyanoborohydride (0.10 g) is added and the reaction is stirred at room temperature for 2 hr. Anhydrous acetone (0.1 ml) is added followed by sodium cyanoborohydride (0.30 g) and the reaction is stirred at room temperature for 2 hr. Concentrated hydrochloric acid is added until the reaction becomes acidic (pH<2). The acidic reaction mixture is evaporated and water is added. Solid potassium hydroxide is added until the solution is pH<10 and sodium chloride is added until the solution is saturated. The latter solution is extracted with ethyl acetate and the organic extract is evaporated. The residue is chromatographed through a column of silica gel using triethylamine-methanol-chloroform (1:1:18). The eluates are evaporated to give a residue (3.06 g) of the title compound, nmr(CDCl$_3$)δ1.2, 1.3, 1.55, 3.7, 4.0 and 6.8–7.5.

In the same manner but replacing acetone with an equivalent amount of butanal, 2-butanone or hexanal, the following compounds of formula I are obtained, respectively: γ-(N-butylaminomethyl)-1-methyl-1,3,4,9-tetrahydropyrano[3,4-b]indole-1-propanol, γ-[N-(1-methylpropyl)aminomethyl]-1-methyl-1,3,4,9-tetrahydropyrano[3,4-b]indole-1-propanol and γ-(N-hexylaminomethyl)-1-methyl-1,3,4,9-tetrahydropyrano[3,4-b]indole-1-propanol.

EXAMPLE 43

γ-[N-Methyl-N-(1-methylethyl)aminomethyl]-1-methyl-1,3,4,9-tetrahydropyrano[3,4-b]indole-1-propanol (I; $R^1$ and $R^5$=$CH_3$; $R^2$, $R^3$, $R^4$ and $R^7$=H; X=O; $R^6$=$CH(CH_3)_2$; $Alk^1$=$CH_2$ and $Alk^2$=$CH_2CH_2$)

Sodium cyanoborohydride (1.0 g, 0.016 mole) is added to a stirred solution of γ-[N-(1-methylethyl)aminomethyl]-1-methyl-1,3,4,9-tetrahydropyrano[3,4-b]indole-1-propanol (described in Example 42, 2.7 g, 0.0085 mole) and 37% aqueous formaldehyde (4 ml, 0.050 mole) in acetonitrile (30 ml). The reaction is stirred for 30 min and acetic acid (0.5 ml) is added dropwise. The reaction is stirred for 2 hr and acetic acid being added occasionally to maintain the pH near neutrality (total volume is 1 ml). The solvent is evaporated and 10% sodium hydroxide is added. The alkaline solution is extracted with ethyl acetate and the organic extract is washed with brine and extracted with 1N hydrochloric acid. The acidic extract is neutralized with solid potassium hydroxide followed by extraction with ethyl acetate. The organic extract is dried over magnesium sulfate and evaporated. Diethyl ether is added to the residue and the precipitate is crystallized from diethyl ether-methanol to obtain the title compound (1.0 g), mp 185°–187° C.

In the same manner but replacing formaldehyde with an equivalent amount of acetaldehyde or butanal, the following compounds of formula I are obtained, respectively: γ-[N-ethyl-N-(1-methylethyl)aminomethyl]-1-methyl-1,3,4,9-tetrahydropyrano[3,4-b]indole-1-propanol and γ-[N-butyl-N-(1-methylethyl)aminomethyl]-1-methyl-1,3,4,9-tetrahydropyrano[3,4-b]indole-1-propanol.

Similarily, replacing γ-[N-(1-methylethyl)aminomethyl]-1-methyl-1,3,4,9-tetrahydropyrano[3,4-b]indole-1-propanol with an equivalent of another compound of formula I described in Example 42, the following compounds of formula I are obtained, respectively: γ-(N-butyl-N-methylaminomethyl)-1-methyl-1,3,4,9-tetrahydropyrano[3,4-b]indole-1-propanol, γ-[N-methyl-N-(1-methylpropyl)aminomethyl]-1-methyl1,3,4,9-tetrahydropyrano[3,4-b]indole-1-propanol and γ-(N-hexyl-N-methylaminomethyl)1-methyl-1,3,4,9-tetrahydropyrano[3,4-b]indole-1-propanol.

EXAMPLE 44

γ-[(Diethylamino)methyl]-1,3,4,9-tetrahydro-1-methylpyrano[3,4-b]indole-1-propanol (I; $R^1$=$CH_3$; $R^2$, $R^3$, $R^4$ and $R^7$=H; $R^5$ and $R^6$=$C_2H_5$; X=O; $Alk^1$=$CH_2$; and $Alk^2$=$CH_2CH_2$)

A solution of γ-aminomethyl-1-methyl-1,3,4,9-tetrahydropyrano[3,4-b]indole-1-propanol (described in Example 41, 2.7 g, 0.001 mole) and ethyl iodide (10 ml) in methanol (20 ml) is stirred at room temperature for 72 hr. The reaction mixture is evaporated to dryness and the residue is partitioned between water and diethyl ether. The aqueous layer is separated, basified with 10% sodium hydroxide and extracted with diethyl ether. The diethyl ether extract is dried over magnesium sulfate, filtered and evaporated. The residue is chromatographed on silica gel using methanol-triethylamine-ethyl acetate (2:2:96) and the eluates are evaporated. The residue is crystallized from a mixture of methanol-ethyl acetate-hexane to obtain the title compound (0.68 g), mp 159°-160° C.

We claim:

1. A compund selected from the group of those of formula VIa

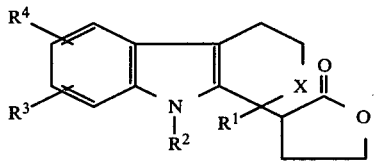

(VIa)

in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; and X is oxa or thia and those of formula IV

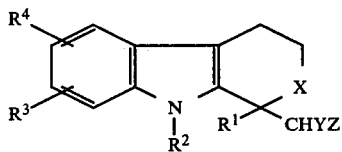

(IV)

in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; X is oxa or thia; Y is selected from the group consisting of:

a. $COOR^8$ wherein $R^8$ is hydrogen or lower alkyl, or a radical of formula $Alk^3$-$COOR^8$ wherein $Alk^3$ is a straight or branched chain lower alkylene having one to five carbon atoms and $R^8$ is as defined herein;

b. $CONR^5R^6$ wherein $R^5$ and $R^6$ each is hydrogen or lower alkyl, or a radical of formula $Alk^3$-$CONR^5R^6$ wherein $Alk^3$, $R^5$ and $R^6$ are as defined herein;

c. a radical of formula $Alk^1$-$NR^5$-$COR^9$ wherein $Alk^1$ is a straight or branched chain lower alkylene having one to six carbon atoms, $R^5$ is as defined herein and $R^9$ is hydrogen or lower alkyl;

d. a radical of formula $Alk^1$-halo wherein $Alk^1$ is as defined herein and halo is chloro, bromo or iodo;

e. a radical of formula $Alk^1$-$NO_2$ wherein $Alk^1$ is as defined herein; and f. a radical of formula $Alk^1$-$NR^5R^6$ wherein $Alk^1$, $R^5$ and $R^6$ are as defined herein;

and Z is selected from the group consisting of:

a. $COOR^{10}$ wherein $R^{10}$ is hydrogen or lower alkyl, or a radical of formula $Alk^4$-$COOR^{10}$ wherein $Alk^4$ is a straight or branched chain lower alkylene having one to five carbon atoms and $R^{10}$ is as defined herein;

b. a radical of formula $Alk^2$-$OCOR^{11}$ wherein $Alk^2$ is a straight or branched chain lower alkylene having one to six carbon atoms and $R^{11}$ is lower alkyl; and c. a radical of formula $Alk^2$-$OR^7$ wherein $Alk^2$ is as defined herein and $R^7$ is hydrogen or lower alkyl with the proviso that when Y is a radical of formula $Alk^1$-$NR^5R^6$ then Z is selected from the group consisting of $COOR^{10}$, and $Alk^2$-$OCOR^{11}$.

2. A compound of formula VIa

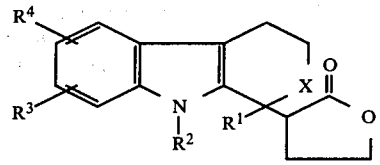

(VIa)

in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; and X is oxa or thia.

3. A compound of formula VIa

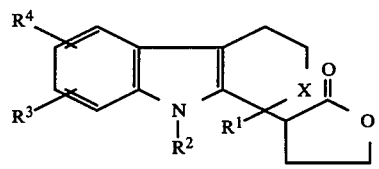

(VIa)

in which $R^1$ is lower alkyl; $R^2$ is hydrogen; $R^3$ and $R^4$ each is hydrogen, lower alkyl or halo; and X is oxa or thia.

4. A compound of formula IV

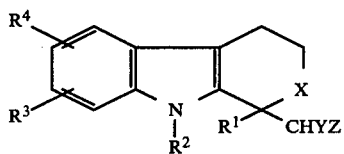

(IV)

in which $R^1$ is lower alkyl; $R^2$ is hydrogen or lower alkyl; $R^3$ and $R^4$ each independently is hydrogen, lower alkyl, halo, nitro, trifluoromethyl or lower alkoxy; X is oxa or thia; Y is selected from the group consisting of:

a. $COOR^8$ wherein $R^8$ is hydrogen or lower alkyl, or a radical of formula $Alk^3$-$COOR^8$ wherein $Alk^3$ is a straight or branched chain lower alkylene having one to five carbon atoms and $R^8$ is as defined herein;

b. $CONR^5R^6$ wherein $R^5$ and $R^6$ each is hydrogen or lower alkyl, or a radical of formula $Alk^3$-$CONR^5R^6$ wherein $Alk^3$, $R^5$ and $R^6$ are as defined herein;

c. a radical of formula $Alk^1$-$NR^5$-$COR^9$ wherein $Alk^1$ is a straight or branched chain lower alkylene having one to six carbon atoms, $R^5$ is as defined herein and $R^9$ is hydrogen or lower alkyl;

d. a radical of formula $Alk^1$-halo wherein $Alk^1$ is as defined herein and halo is chloro, bromo or iodo;

e. a radical of formula $Alk^1$-$NO_2$ wherein $Alk^1$ is as defined herein; and f. a radical of formula $Alk^1$-$NR^5R^6$ wherein $Alk^1$, $R^5$ and $R^6$ are as defined herein;

and Z is selected from the group consisting of:

a. $COOR^{10}$ wherein $R^{10}$ is hydrogen or lower alkyl, or a radical of formula $Alk^4$-$COOR^{10}$ wherein $Alk^4$ is a straight or branched chain lower alkylene having one to five carbon atoms and $R^{10}$ is as defined herein;

b. a radical of formula $Alk^2$-$OCOR^{11}$ wherein $Alk^2$ is a straight or branched chain lower alkylene having one to six carbon atoms and $R^{11}$ is lower alkyl; and c. a radical of formula Alk$^2$-OR$^7$ wherein Alk$^2$ is as defined herein and R$^7$ is hydrogen or lower alkyl with the proviso that when Y is a radical of formula Alk$^1$-NR$^5$R$^6$ then Z is selected from the group consisting of COOR$^{10}$, and Alk$^2$-OCOR$^{11}$.

5. A compound of formula IVa

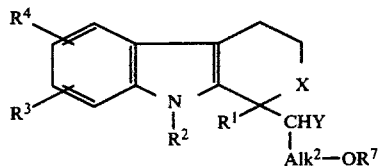

in which R$^1$ is lower alkyl; R$^2$ is hydrogen or lower alkyl; R$^3$ and R$^4$ each independently is hydrogen, lower alkyl, halo, nitro, trifluoromethyl or lower alkoxy; R$^7$ is hydrogen; Alk$^2$ is a straight or branched chain lower alkylene having one to six carbon atoms; X is oxa or thia, and Y is CONR$^5$R$^6$ wherein R$^5$ and R$^6$ each is hydrogen or lower alkyl or a radical of formula Alk$^3$-CONR$^5$R$^6$ wherein Alk$^3$ is a straight or branched chain lower alkylene having one to five carbon atoms and R$^5$ and R$^6$ are as defined herein.

6. A compound of formula IVb

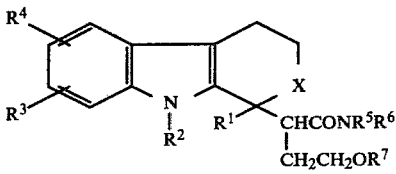

in which R$^1$ is lower alkyl; R$^2$ is hydrogen or lower alkyl; R$^3$ and R$^4$ are hydrogen; R$^5$ is lower alkyl; R$^6$ is hydrogen or lower alkyl; R$^7$ is hydrogen or lower alkyl; and X is oxa or thia.

7. A compound of formula IVb, as claimed in claim 6, wherein R$^1$, R$^3$, R$^4$, R$^5$ and R$^6$ are as defined therein; R$^2$ and R$^7$ are hydrogen and X is oxa.

* * * * *